US011760719B2

United States Patent
Pai et al.

(10) Patent No.: US 11,760,719 B2
(45) Date of Patent: Sep. 19, 2023

(54) DIAMINE COMPOSITION, AND METHOD OF PREPARING DIISOCYANATE COMPOSITION

(71) Applicants: SKC CO., LTD., Gyeonggi-do (KR); WOORI FINE CHEM CO., LTD., Gyeonggi-do (KR)

(72) Inventors: Jaeyoung Pai, Gyeonggi-do (KR); Jeongmoo Kim, Gyeonggi-do (KR); Hyuk Hee Han, Gyeonggi-do (KR); Jung Hwan Myung, Gyeonggi-do (KR); Jooyoung Jung, Gyeonggi-do (KR); Myung-Ok Kyun, Gyeonggi-do (KR)

(73) Assignees: SKC CO., LTD., Gyeonggi-do (KR); WOORI FINE CHEM CO., LTD., Gyeonggi-do (KR)

( * ) Notice: Subject to any disclaimer, the term of this patent is extended or adjusted under 35 U.S.C. 154(b) by 31 days.

(21) Appl. No.: 17/111,779

(22) Filed: Dec. 4, 2020

(65) Prior Publication Data
US 2021/0171447 A1 Jun. 10, 2021

(30) Foreign Application Priority Data

Dec. 6, 2019 (KR) .................. 10-2019-0161450
Dec. 6, 2019 (KR) .................. 10-2019-0162101
May 6, 2020 (KR) .................. 10-2020-0054128

(51) Int. Cl.
  *C07C 263/20* (2006.01)
  *C07C 263/10* (2006.01)
  (Continued)

(52) U.S. Cl.
  CPC .......... *C07C 263/20* (2013.01); *C07C 211/27* (2013.01); *C07C 263/10* (2013.01); *C07C 265/14* (2013.01)

(58) Field of Classification Search
None
See application file for complete search history.

(56) References Cited

U.S. PATENT DOCUMENTS 2,379,948 A * 7/1945 Burgoine .............. C07C 263/10
  564/462
2003/0013917 A1 1/2003 Nakamura et al.
(Continued)

FOREIGN PATENT DOCUMENTS

CN 1931834 * 3/2007
CN 1931834 A 3/2007
(Continued)

OTHER PUBLICATIONS

Austin ("Hydrochloric Acid" Ullmann's Encyclopedia of Industrial Chemistry, first published Jun. 15, 2000, p. 191-205, downloaded from https://doi.org/10.1002/14356007.a13_283 on Jul. 28, 2022) (Year: 2000).*

(Continued)

*Primary Examiner* — Amy C Bonaparte
(74) *Attorney, Agent, or Firm* — IP&T Group LLP

(57) ABSTRACT

A diamine composition comprising a benzylmonoamine having a methyl group in an amount of 10 ppm to 2,000 ppm in the composition and use thereof for the preparation of a diisocyanate composition and an optical material. A process for preparing a diisocyanate composition wherein the b* value according to the CIE color coordinate of the diamine composition is adjusted to a specific range, whereby the yield and purity of the diisocyanate composition and the optical characteristics of the final optical lens are enhanced. Use of the process for the diisocyanate composition for preparing a plastic optical lens of high quality.

4 Claims, 1 Drawing Sheet

(51) Int. Cl.
*C07C 211/27* (2006.01)
*C07C 265/14* (2006.01)

(56) References Cited

U.S. PATENT DOCUMENTS

| | | | |
|---|---|---|---|
| 2009/0020407 A1 | 1/2009 | Hugo et al. | |
| 2009/0192334 A1 | 7/2009 | Amakawa | |
| 2018/0334531 A1* | 11/2018 | Shin | G02B 1/041 |
| 2019/0292304 A1 | 9/2019 | Yamasaki et al. | |
| 2021/0230352 A1* | 7/2021 | Kim | C08G 18/3876 |

FOREIGN PATENT DOCUMENTS

| | | | | |
|---|---|---|---|---|
| CN | 106674056 | * | 5/2017 | C07C 263/10 |
| CN | 106674056 A | | 5/2017 | |
| CN | 106748887 A | | 5/2017 | |
| JP | S61-194057 A | | 8/1986 | |
| JP | H05-246973 A | | 9/1993 | |
| JP | H08-034774 A | | 2/1996 | |
| JP | 2003-026639 A | | 1/2003 | |
| JP | 2009-525303 A | | 7/2009 | |
| JP | 2018-070611 A | | 5/2018 | |
| KR | 1994-0001948 B1 | | 3/1994 | |
| KR | 2018-0125871 A | | 11/2018 | |
| WO | 2006/001298 A1 | | 1/2006 | |
| WO | 2018/190290 A1 | | 10/2018 | |
| WO | WO-2019235862 A1 | * | 12/2019 | C07C 209/00 |

OTHER PUBLICATIONS

Morioka ("Selective hydrogenation of arenes to cyclohexanes in water catalyzed by chitin-supported ruthenium nanoparticles" Catalysis Science and Technology, 2016, p. 5801-5805; including Supporting Information p. S1-S48) (Year: 2016).*

Office Action issued by the Korean Patent Office dated May 25, 2021.

Office Action issued by the Korean Patent Office dated Nov. 26, 2020.

Office Action issued by the Korean Intellectual Property Office dated Jan. 26, 2022.

Office Action issued by the Japanese Patent Office dated Dec. 21, 2021.

* cited by examiner

[Fig. 1A]
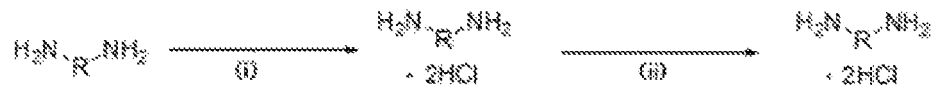
[Fig. 1B]
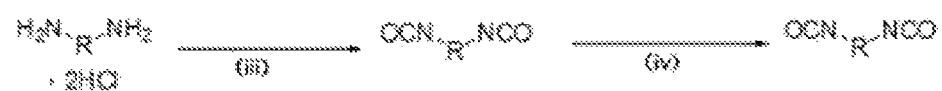
[Fig. 2]
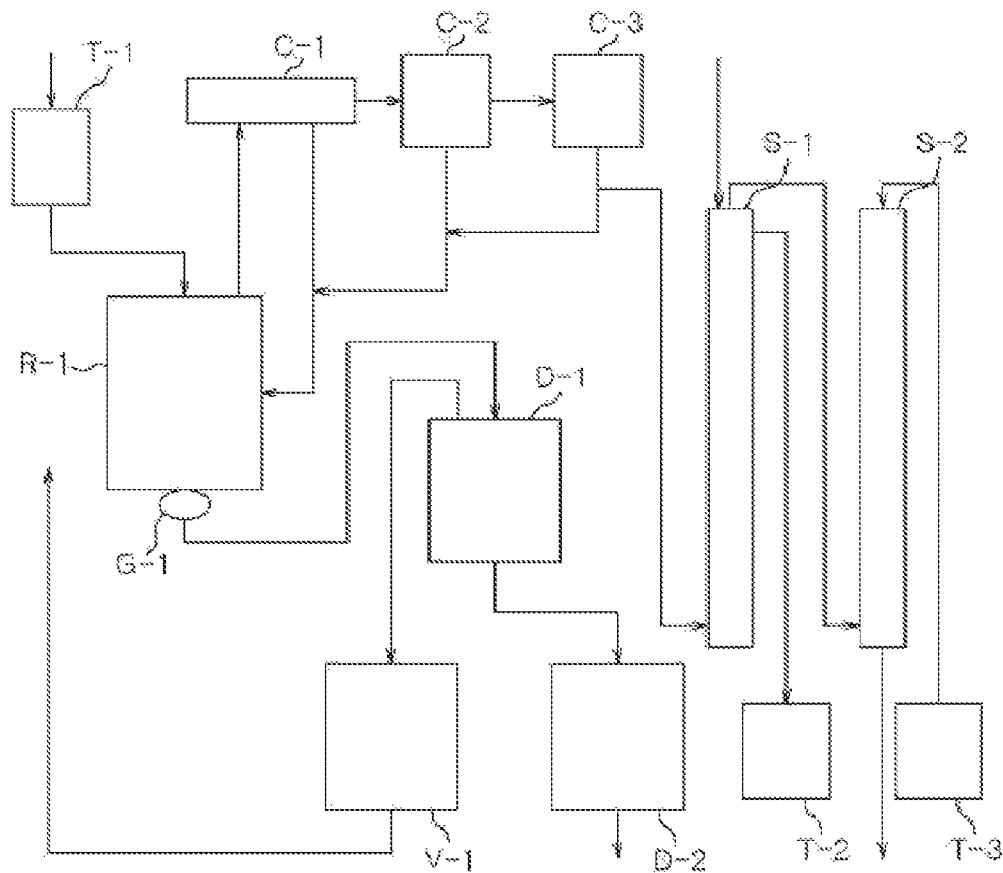

DIAMINE COMPOSITION, AND METHOD OF PREPARING DIISOCYANATE COMPOSITION

The present application claims priority of Korean patent application numbers 10-2019-0161450 filed on Dec. 6, 2019, Korean patent application numbers 10-2019-0162101 filed on Dec. 6, 2019 and Korean patent application numbers 10-2020-0054128 filed on May 6, 2020. The disclosure of each of the foregoing applications is incorporated herein by reference in its entirety.

TECHNICAL FIELD

Embodiments relate to a diamine composition and a process for preparing a diisocyanate composition. Specifically, the embodiments relate to a diamine composition and a process for preparing a diisocyanate composition using the same.

BACKGROUND ART

Since plastics optical materials are lightweight, hardly breakable, and excellent in dyeability as compared with optical materials made of inorganic materials such as glass, is plastic materials of various resins are widely used as optical materials for eyeglass lenses, camera lenses, and the like. In recent years, there has been an increased demand for higher performance of optical materials, particularly in terms of high transparency, high refractive index, low specific gravity, high thermal resistance, high impact resistance, and the like.

Polythiourethanes are widely used as an optical material by virtue of their excellent optical characteristics and excellent mechanical properties. A polythiourethane may be prepared by reacting a thiol and an isocyanate. Lenses made from a polythiourethane are widely used by virtue of their high refractive index, lightweight, and relatively high impact resistance.

Isocyanates used as a raw material of a polythiourethane are capable of producing polythiourethanes having different structures depending on the number and position of the functional groups in the isocyanates. Thus, the isocyanates have a significant impact on the physical properties of a product produced from the polythiourethane. Accordingly, a certain kind of isocyanate that can impart the desired properties to a final product is used.

In particular, since xylylene diisocyanate (XDI) has both characteristics of alicyclic isocyanates (e.g., resistance to yellowing, readily controllable reactivity, and the like) and those of aliphatic isocyanates (e.g., excellent mechanical properties, high refractive indices, and the like), it is advantageously used as an optical material.

The xylylene diisocyanate is classified into orthoxylylene diisocyanate (o-XDI), metaxylylene diisocyanate (m-XDI), and paraxylylene diisocyanate (p-XDIA) depending on the relative position of the diisocyanate groups. m-XDI among these is the most widely used as a raw material for an optical lens since it is suitable for the physical properties of an optical lens and available in the market.

However, even when m-XDI is used for an optical material, there is a limit in achieving satisfactory optical characteristics due to the occurrence of striae, cloudiness, or yellowing in the optical material. Even if the optical characteristics in terms of stria, cloudiness, or yellow index are satisfied, the impact resistance may be deteriorated. Thus, it is still difficult to satisfy them at the same time.

Accordingly, in order to achieve an optical material of high quality by simultaneously enhancing the optical characteristics and mechanical characteristics, there is an urgent demand for developing a composition having a specific range of composition or a process for preparing the same.

In addition, isocyanates used as a raw material for plastic optical lenses are prepared by a phosgene method, a non-phosgene method, a pyrolysis method, or the like.

In the phosgene method, an amine as a raw material is reacted with phosgene ($COCl_2$) gas to synthesize an isocyanate. In addition, in the non-phosgene method, xylylene chloride is reacted with sodium cyanate in the presence of a catalyst to synthesize an isocyanate. In the pyrolysis method, an amine is reacted with an alkyl chloroformate to prepare a carbamate, which is pyrolyzed in the presence of a catalyst at a high temperature to synthesize an isocyanate.

The phosgene method among the above methods for preparing isocyanates is the most widely used. In particular, a direct method in which an amine is directly reacted with phosgene gas has been commonly used. But it has a problem that a plurality of apparatuses for the direct reaction of phosgene gas are required. Meanwhile, in order to supplement the direct method, a hydrochloride method has been developed in which an amine is reacted with hydrogen chloride gas to obtain an amine hydrochloride as an intermediate, which is reacted with phosgene, as disclosed in Korean Patent Publication No. 1994-0001948.

However, in the method of obtaining hydrochloride as an intermediate by reacting an amine with hydrogen chloride gas among the conventional phosgene methods for synthesizing isocyanates, a hydrochloride is produced as fine particles at atmospheric pressure, so that the agitation inside the reactor is not smoothly carried out. Thus, an additional process of raising the temperature to increase the pressure inside the reactor is required, and there is a problem that the yield of the final product is low as well.

Thus, an attempt has been made to obtain a hydrochloride using an aqueous hydrochloric acid solution instead of hydrogen chloride gas. However, as the amine is dissolved in the aqueous hydrochloric acid solution, the yield is significantly reduced to 50%, making it difficult to be applied in practice. There is a difficulty in that an amine having a low content of water and impurities should be used as a raw material in order to increase the purity of the final product. In addition, phosgene gas used in the conventional phosgene method is highly toxic and is a substance subject to environmental regulations. There is a difficulty in storage and management since a separate cooling apparatus is required to store it.

DETAILED DESCRIPTION OF THE INVENTION

Technical Problem

The present invention is designed to solve the problems of the prior art. It has been discovered that the physical properties of an optical material can be effectively satisfied using a diamine composition when a benzylmonoamine having a methyl group is employed in a specific amount in the diamine composition.

Accordingly, an object of the embodiments is to provide a diamine composition in which the content of a benzylmonoamine having a methyl group is adjusted in the composition, thereby preventing the occurrence of striae and cloudiness of an optical material while enhancing the impact resistance.

In addition, the present inventors have been able to solve the conventional environmental, yield, and quality problems in the process of preparing a diisocyanate, which is mainly used as a raw material for plastic optical lenses, from a diamine composition through a hydrochloride thereof by way of using an aqueous hydrochloric acid solution and an organic solvent instead of hydrogen chloride gas and solid triphosgene instead of phosgene gas while adjusting the reaction conditions.

In addition, the present inventors have focused that the diamine in a diamine composition is oxidized to form a double bond during the storage thereof, as a result, the purity and yield of a diisocyanate composition prepared using the same may be lowered, and it may cause cloudiness and yellowing in the final optical lens. In particular, the present inventors have focused that the b* value according to the CIE color coordinate of a diamine composition is related to the degree of oxidation of the diamine composition.

As a result of research conducted by the present inventors, it has been discovered that if the b* value according to the CIE color coordinate of a diamine composition used in the preparation of a diisocyanate composition is adjusted to a specific range, it is possible to enhance not only the yield and purity of the diisocyanate composition but also the optical characteristics of the final optical lens.

Accordingly, an object of the embodiments is to provide a process for preparing a diisocyanate composition whose purity and yield are enhanced using a diamine composition in which the b* value according to the CIE color coordinate is adjusted, and a process for preparing an optical lens whose optical characteristics are enhanced.

Solution to the Problem

According to an embodiment, there is provided a diamine composition, which comprises a diamine; and a benzylmonoamine having a methyl group in an amount of 10 ppm to 2,000 ppm.

According to another embodiment, there is provided a process for preparing a diisocyanate composition, which comprises reacting a diamine composition with an aqueous hydrochloric acid solution to obtain a diamine hydrochloride composition; and obtaining a diisocyanate composition using the diamine hydrochloride composition and triphosgene, wherein the diamine composition comprises a diamine; and a benzylmonoamine having a methyl group in an amount of 10 ppm to 2,000 ppm.

According to still another embodiment, there is provided a process for preparing a diisocyanate composition, which comprises reacting a diamine composition with an aqueous hydrochloric acid solution to obtain a diamine hydrochloride composition; and obtaining a diisocyanate composition using the diamine hydrochloride composition and triphosgene, wherein the diamine composition has a b* value according to the CIE color coordinate of 0.01 to 3.0.

Advantageous Effects of the Invention

According to the embodiments, a diamine composition comprising a benzylmonoamine having a methyl group in a specific amount is used, whereby it is possible to adjust the composition of a diisocyanate composition used in the production of a polythiourethane-based optical lens. Thus, an optical lens of high quality can be prepared.

That is, in order to achieve an optical material of high quality, a diamine composition comprising a benzylmonoamine having a methyl group in a specific amount is used, thereby improving the optical characteristics by preventing the occurrence of yellowing, striae, and cloudiness and enhancing the mechanical properties such as impact resistance at the same time.

In addition, if the b* value according to the CIE color coordinate of a diamine composition used in the preparation of a diisocyanate composition is adjusted to a specific range, it is possible to enhance not only the yield and purity of the diisocyanate composition but also the optical characteristics of the final optical lens. Specifically, the b* value may be adjusted within a specific range to control the degree of oxidation of the diamine present in a diamine composition; as a result, it is possible to suppress side reactions in the process for preparing a diisocyanate composition.

In addition, in the process for preparing a diisocyanate composition according to a preferable embodiment, an aqueous hydrochloric acid solution, without the use of hydrogen chloride gas, is used to prepare a diamine hydrochloride as an intermediate. Since the reaction can be carried out even at atmospheric pressure, an additional apparatus for high-temperature heating and cooling is not required, and the yield can be enhanced.

In addition, in the process for preparing a diisocyanate composition, an aqueous hydrochloric acid solution and an organic solvent are used, while the reaction conditions are adjusted, to prepare a diamine hydrochloride composition, so that the final yield can be further enhanced by preventing the hydrochloride from being dissolved in the aqueous hydrochloric acid solution. The selection of raw materials can be broadened since the content of water and impurities in the diamine composition as a raw material has little impact. In addition, phosgene gas, which is highly toxic and has difficulties in storage and management, is not used. Instead, triphosgene, which is less toxic and does not require a separate cooling storage apparatus since it is solid at room temperature, is used; thus, it is excellent in the handling convenience and processability.

Accordingly, the process for preparing a diisocyanate composition according to the embodiment can be applied to the preparation of a plastic optical lens of high quality.

BRIEF DESCRIPTION OF THE DRAWINGS

FIG. 1A and FIG. 1B schematically show the process for preparing a diisocyanate composition according to an embodiment.

FIG. 2 shows an example of the process equipment for the reaction of a diamine hydrochloride and triphosgene.

REFERENCE NUMERALS OF THE DRAWINGS

T-1: first tank,
T-2: second tank,
T-3: third tank
R-1: reactor,
D-1: first distiller,
D-2: second distiller
C-1: first condenser,
C-2: second condenser,
C-3: third condenser
S-1: first scrubber,
S-2: second scrubber
G-1: viewing window,
V-1: solvent recovery apparatus.

BEST MODE FOR CARRYING OUT THE INVENTION

Throughout the present specification, when a part is referred to as "comprising" an element, it is understood that other elements may be comprised, rather than other elements are excluded, unless specifically stated otherwise.

In addition, all numbers and expression related to the physical properties, contents, dimensions, and the like used herein are to be understood as being modified by the term "about," unless otherwise indicated.

In the present specification, an "amine" refers to a compound having one or more amine groups at the terminal, and a "diamine" refers to a compound having two amine groups at the terminal. They may have a wide variety of structures depending on the skeleton of an aliphatic chain, an aliphatic ring, and an aromatic ring. Specific examples of the diamine include xylylenediamine (XDA), hexamethylenediamine (HDA), 2,2-dimethylpentanediamine, 2,2,4-trimethylhexanediamine, butanediamine, 1,3-butadiene-1,4-diamine, 2,4,4-trimethylhexamethylenediamine, bis(aminoethyl)carbonate, 4,4'-methylenediamine (MDA), bis(aminoethyl) ether, bis(aminoethyl)benzene, bis(aminopropyl)benzene, α,α,α',α'-tetramethylxylylenediamine, bis(aminobutyl)benzene, bis(aminomethyl)naphthalene, bis(aminomethyl)diphenyl ether, bis(aminoethyl)phthalate, 2,6-di(aminomethyl)furan, hydrogenated xylylenediamine (H6XDA), dicyclohexylmethanediamine, cyclohexanediamine, methylcyclohexanediamine, isophoronediamine (IPDA), dicyclohexyldimethylmethanediamine, 2,2-dimethyldicyclohexylmethanediamine, 2,5-bis(aminomethyl)bicyclo-[2,2,1]-heptane, 2,6-bis(aminomethyl)bicyclo-[2,2,1]-heptane, 3,8-bis(aminomethyl)tricyclodecane, 3,9-bis(aminomethyl)tricyclodecane, 4,8-bis(aminomethyl)tricyclodecane, 4,9-bis(aminomethyl)tricyclodecane, norbornenediamine (NBDA), bis(aminomethyl) sulfide, bis(aminoethyl) sulfide, bis(aminopropyl) sulfide, bis(aminohexyl) sulfide, bis(aminomethyl) sulfone, bis(aminomethyl)disulfide, bis(aminoethyl) disulfide, bis(aminopropyl) disulfide, bis(aminomethylthio) methane, bis(aminoethylthio)methane, bis(aminoethylthio) ethane, and bis(aminomethylthio)ethane. More specifically, the diamine may be at least one selected from the group consisting of xylylenediamine (XDA), norbornenediamine (NBDA), hydrogenated xylylenediamine (H6XDA), isophoronediamine (IPDA), and hexamethylenediamine (HDA). The xylylenediamine (XDA) includes orthoxylylenediamine (o-XDA), metaxylylenediamine (m-XDA), and paraxylylenediamine (p-XDA).

In the present specification, an "isocyanate" refers to a compound having an NCO group, a "diisocyanate" refers to a compound having two NCO groups at the terminal. They may have a wide variety of structures depending on the skeleton of an aliphatic chain, an aliphatic ring, and an aromatic ring. Specific examples of the diamine include xylylene diisocyanate (XDI), hexamethylene diisocyanate (HDI), 2,5-bis(isocyanatomethyl)-bicyclo[2.2.1]heptane, 2,6-bis(isocyanatomethyl)-bicyclo[2.2.1]heptane, hydrogenated xylylene diisocyanate (H6XDI), dicyclohexylmethane diisocyanate, isophorone diisocyanate (IPDI), 1,2-diisocyanatobenzene, 1,3-diisocyanatobenzene, 1,4-diisocyanatobenzene, 2,4-diisocyanatotoluene, ethylphenylene diisocyanate, dimethylphenylene diisocyanate, biphenyl diisocyanate, toluidine diisocyanate, 4,4'-methylenebis(phenylisocyanate) (MDI), 1,2-bis(isocyanatomethyl)benzene, 1,3-bis(isocyanatomethyl)benzene, 1,4-bis(isocyanatomethyl)benzene, 1,2-bis(isocyanatoethyl)benzene, 1,3-bis(isocyanatoethyl)benzene, 1,4-bis(isocyanatoethyl)benzene, α,α,α',α'-tetramethylxylylene diisocyanate, bis(isocyanatomethyl)naphthalene, bis(isocyanatomethylphenyl) ether, norbornene diisocyanate (NBDI), bis(isocyanatoethyl) sulfide, bis(isocyanatoethyl) sulfide, bis(isocyanatopropyl) sulfide, 2,5-diisocyanatotetrahydrothiophene, 2,5-diisocyanatomethyltetrahydrothiophene, 3,4-diisocyanatomethyltetrahydrothiophene, 2,5-diisocyanato-1,4-dithiane, and 2,5-diisocyanatomethyl-1,4-dithiane. More specifically, the diisocyanate may be at least one selected from the group consisting of xylylene diisocyanate (XDI), norbornene diisocyanate (NBDI), hydrogenated xylylene diisocyanate (H6XDI), isophorone diisocyanate (IPDI), and hexamethylene diisocyanate (HDI). The xylylene diisocyanate (XDI) includes orthoxylylene diisocyanate (o-XDI), metaxylylene diisocyanate (m-XDI), and paraxylylene diisocyanate (p-XDIA).

In the present specification, as is well known, a "composition" may refer to a form in which two or more chemical components are mixed or combined in a solid, liquid, and/or gas phase while generally maintaining their respective unique properties.

The compounds used in each reaction step according to the above embodiment (e.g., triphosgene) or the compounds obtained as a result of the reaction (e.g., diamine hydrochloride, diisocyanate) are generally present in a mixed or combined state with heterogeneous components generated as unreacted raw materials in each reaction step, as side reactions or reaction with water, or as natural decomposition of the compounds. A trace amount of these components may remain to exist with the main components.

According to the embodiment, since attention is paid to these heterogeneous components mixed or combined with the main compounds, even a trace amount of the heterogeneous components is treated as a composition mixed or combined with the main compounds to specifically illustrate the components and contents thereof.

In addition, in the present specification, for clear and easy distinction between various compositions, terms are also described in combination with the names of the main components in the composition. For example, a "diamine hydrochloride composition" refers to a composition comprising a diamine hydrochloride as a main component, and a "diisocyanate composition" refers to a composition comprising a diisocyanate as a main component. In such event, the content of the main component in the composition may be 50% by weight or more, 80% by weight or more, or 90% by weight or more, for example, 90% by weight to 99.9% by weight.

In this specification, the unit of ppm refers to ppm by weight.

[Diamine Composition]

The diamine composition according to an embodiment comprises a diamine; and a benzylmonoamine having a methyl group in an amount of 10 ppm to 2,000 ppm.

According to an embodiment of the present invention, the benzylmonoamine having a methyl group may be intentionally added to the diamine composition.

In addition, the benzylmonoamine having a methyl group may be produced during the process for preparing the diamine composition.

In addition, the benzylmonoamine having a methyl group may be produced during the process for preparing the diisocyanate composition, and a part thereof may be intentionally added. That is, the benzylmonoamine having a methyl group may be produced during the process for preparing the diisocyanate composition. If the amount thus produced is not sufficient, it may be intentionally added to the composition such that the content thereof is 10 ppm to 2,000 ppm in the composition.

According to an embodiment of the present invention, a diamine composition comprising a benzylmonoamine having a methyl group in a specific amount is used, whereby, when used for the preparation of a diisocyanate composition and an optical material, it is possible to improve the optical characteristics by preventing the occurrence of yellowing, striae, and cloudiness in the optical material and to enhance the mechanical properties such as impact resistance at the same time.

Specifically, if the diamine composition comprises a benzylmonoamine having a methyl group in a specific amount, the diisocyanate composition prepared using the same may comprise a specific component having one isocyanate functional group, that is, a benzyl isocyanate having a methyl group in a specific amount.

In addition, when a diisocyanate composition comprising a benzyl isocyanate having a methyl group in a specific amount is used with a thiol or an episulfide in the polythiourethane reaction to prepare an optical material, the benzyl isocyanate having a methyl group has one isocyanate functional group in the polyurethane reaction, it may stop the crosslinking reaction, thereby promoting the enhancement in the flexibility of the polythiourethane. Thus, if an optical material such as an optical lens is prepared using the same, it is possible to prevent the occurrence of striae and cloudiness and to enhance the impact resistance at the same time.

According to an embodiment of the present invention, the benzylmonoamine having a methyl group may comprise a benzylmonoamine having a methyl group with a specific aromatic structure. Specifically, it may comprise at least one selected from the group consisting of 2-methylbenzylamine substituted with a methyl group at the ortho (o) position, 3-methylbenzylamine substituted with a methyl group at the meta (m) position, and 4-methylbenzylamine substituted with a methyl group at the para (p) position.

For example, the benzylmonoamine having a methyl group may comprise at least one selected from the group consisting of 3-methylbenzylamine substituted with a methyl group at the meta (m) position and 4-methylbenzylamine substituted with a methyl group at the para (p) position.

In addition, the benzylmonoamine having a methyl group may comprise at least one selected from the group consisting of 3-methylbenzylamine substituted with a methyl group at the meta (m) position and 2-methylbenzylamine substituted with a methyl group at the ortho (o) position.

More specifically, the benzylmonoamine having a methyl group may comprise a compound of the following Formula 1 in which a methyl group is substituted at the meta (m) position.

[Formula 1]

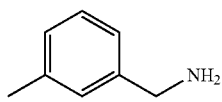

According to an embodiment of the present invention, the content of the benzylmonoamine having a methyl group contained in the diamine composition may be 10 ppm to 2,000 ppm, 100 ppm to 2,000 ppm, 500 ppm to 2,000 ppm, 500 ppm to 1,000 ppm, 1,000 ppm to 2,000 ppm, 10 ppm to 1,500 ppm, 10 ppm to 1,000 ppm, 10 ppm to 800 ppm, 10 ppm to 500 ppm, 10 ppm to 300 ppm, or 10 ppm to 100 ppm. The content of the benzylmonoamine having a methyl group contained in the composition is adjusted within the above range, whereby it is possible to enhance the impact resistance and to prevent the occurrence of striae and cloudiness at the same time when an optical material is prepared therefrom.

If the content of the benzylmonoamine having a methyl group is not adjusted, the impact resistance of the optical material may be deteriorated, and striae and cloudiness may occur even if the impact resistance is maintained. For example, if the content of the benzylmonoamine having a methyl group is less than 10 ppm, the impact resistance of the optical material prepared using the diamine composition may be deteriorated. On the other hand, if the content of the benzylmonoamine having a methyl group exceeds 2,000 ppm, striae or cloudiness may occur even if the impact resistance of the optical material prepared using the diamine composition is enhanced.

Meanwhile, the diamine composition may comprise 99% by weight to less than 100% by weight of a diamine based on the total weight of the composition. For example, the content of a diamine in the diamine composition may be 90% by weight or more, 95% by weight or more, 99.5% by weight or more, or 99.9% by weight or more, specifically 90% to 99.9% by weight.

The diamine may comprise xylylenediamine. The xylylenediamine may comprise at least one selected from the group consisting of orthoxylylenediamine (o-XDA), metaxylylenediamine (m-XDA), and paraxylylenediamine (p-XDA).

The diamine composition according to an embodiment may comprise metaxylylenediamine (m-XDA) in an amount of 99% by weight to less than 100% by weight, for example, 99.5% by weight to less than 100% by weight or 99.7% by weight to less than 100% by weight.

If metaxylylenediamine is contained in the composition in an amount less than the above range, when a diisocyanate composition is prepared using the same, the content of metaxylylene diisocyanate, which may be produced by the reaction with an aqueous hydrochloric acid solution, may decrease according to the content of metaxylylenediamine. In such event, not only the optical characteristics (especially, striae, transmittance, and the like) but also the mechanical properties (such as impact resistance, tensile strength, and the like) of the final product may be impaired due to the nonuniformity in the polymerization reactivity of the composition and in the chemical structure of the cured product. Further, yellowing may occur depending on other components incorporated therein.

According to an embodiment, the diamine composition may comprise the compound of Formula 1 in an amount of 100 ppm to 2,000 ppm and metaxylylenediamine in an amount of 99.5% by weight to less than 100% by weight based on the total weight of the composition.

In addition, paraxylylenediamine may be contained in an amount of greater than 0% by weight to 0.5% by weight, greater than 0% by weight to 0.3% by weight, greater than 0% by weight to 0.15% by weight, greater than 0% by weight to 0.1% by weight, greater than 0% by weight to 0.05% by weight, greater than 0% by weight to 0.03% by weight, or greater than 0% by weight to 0.01% by weight, based on the total weight of the composition.

If paraxylylenediamine is contained in the composition in an amount exceeding the above range, when a diisocyanate composition is prepared using the same, the content of paraxylylene diisocyanate, which may be produced by the reaction with an aqueous hydrochloric acid solution, may excessively increase according to the content of paraxylylenediamine. In such event, the optical characteristics may be impaired as striae occur or the transmittance is lowered due to the nonuniform polymerization caused by differences in the reactivity or due to the crystallization caused by changes in the chemical structure of the polymer.

Therefore, a product produced using the diamine composition whose composition has been adjusted as described above can satisfy excellent optical characteristics, and it is possible to achieve excellent mechanical properties. Thus, it can be advantageously used for the production of optical materials, specifically plastic optical lenses.

In particular, according to the embodiment, the b* value according to the CIE color coordinate of the diamine composition is adjusted within a range of 0.01 to 3.0.

If the b* value according to the CIE color coordinate of a diamine composition is adjusted to a specific range, it is possible to enhance not only the yield and purity of the diisocyanate composition but also the optical characteristics of the final optical lens. Specifically, the diamine in a diamine composition is oxidized to form a double bond during the storage thereof a; as a result, the color and haze of a diisocyanate composition prepared using the same may be deteriorated, and it may cause striae and yellowing in the final optical lens. The degree of oxidation of a diamine composition is related to the b* value according to the CIE color coordinate of the diamine composition. Thus, the b* value may be adjusted within a specific range to control the degree of oxidation of the diamine present in a diamine composition; as a result, it is possible to suppress side reactions in the process for preparing a diisocyanate composition.

For example, the b* value according to the CIE color coordinate of the diamine composition may be 0.01 or more, 0.1 or more, 0.3 or more, 0.5 or more, 0.7 or more, 1.0 or more, 1.3 or more, or 1.5 or more. In addition, the b* value may be 3.0 or less, 2.5 or less, 2.0 or less, 1.5 or less, or 1.0 or less. For example, the diamine composition may have a b* value according to the CIE color coordinate of 0.01 to 1.0. Specifically, the b* value according to the CIE color coordinate of the diamine composition may be 0.1 to 3.0, 0.1 to 2.5, 0.1 to 2.0, 0.1 to 1.5, 0.1 to 1.0, 0.5 to 3.0, 1.0 to 3.0, or 1.5 to 3.0.

The b* value according to the CIE color coordinate of the diamine composition may be adjusted in advance before the diamine composition is introduced to the reaction. For example, the b* value according to the CIE color coordinate of the diamine composition is measured in advance. If the b* value thus measured exceeds 3.0, the b* value of the diamine composition may be adjusted and then introduced to the reaction.

That is, the process for preparing a diisocyanate composition according to still another embodiment may further comprise measuring the b* value according to the CIE color coordinate of the diamine composition before the step of obtaining the diamine composition; and adjusting the b* value to 0.01 to 3.0.

The b* value may be measured using a spectrophotometer or the like. Specifically, a liquid sample may be filled in a quartz cell having a thickness of 10 mm, and a solid sample may be dissolved in an organic solvent to measure the b* value.

The method of adjusting the b* value is not particularly limited. For example, it may comprise distilling the diamine composition at least once.

The temperature during distillation of the diamine composition may be, for example, 100° C. to 130° C. Specifically, the distillation may be carried out by setting the bottom temperature of the distiller to 100° C. to 130° C. For example, the distillation may be carried out by setting the reboiler temperature to 100° C. to 130° C.

In addition, the pressure during the distillation of the diamine composition may be 2.0 torr or less, 1.0 torr or less, 0.5 torr or less, or 0.1 torr or less.

Specifically, the distillation of the diamine composition may be carried out under the conditions of, for example, a temperature of 100° C. to 130° C. and a pressure of 0.1 Torr to 1 Torr. Within the above preferred range, it is possible to effectively remove oxides such as a diamine in which a double bond has been formed during the storage of a diamine composition.

In addition, the time for the distillation may be 1 hour or longer, 2 hours or longer, or 3 hours or longer, and may be 10 hours or shorter or 5 hours or shorter.

A step of measuring the b* value according to the CIE color coordinate of the diamine composition may be further carried out upon the distillation as described above. If the b* value thus measured exceeds 3.0, the b* value of the diamine composition may be adjusted by carrying out the distillation once again.

As a result, the b* value according to the CIE color coordinate of the diamine composition may be adjusted to 0.01 to 3.0.

[Process for Preparing a Diisocyanate Composition]

A diisocyanate composition may be prepared using a diamine composition whose composition has been adjusted according to an embodiment of the present invention.

The process for preparing a diisocyanate composition according to another embodiment comprises reacting a diamine composition with an aqueous hydrochloric acid solution to obtain a diamine hydrochloride composition; and obtaining a diisocyanate composition using the diamine hydrochloride composition and triphosgene, wherein the diamine composition comprises a diamine; and a benzylmonoamine having a methyl group in an amount of 10 ppm to 2,000 ppm.

According to still another embodiment, there is provided a process for preparing a diisocyanate composition, which comprises reacting a diamine composition with an aqueous hydrochloric acid solution to obtain a diamine hydrochloride composition; and obtaining a diisocyanate composition using the diamine hydrochloride composition and triphosgene, wherein the diamine composition has a b* value according to the CE color coordinate of 0.01 to 3.0.

FIG. 1A and FIG. 1B schematically show the process for preparing a diisocyanate composition according to an embodiment. In FIG. 1A and FIG. 1B, R comprises an aromatic ring, an aliphatic ring, an aliphatic chain, and the like. As a specific example, R may be xylylene, norbornene, hydrogenated xylylene, isophorone, or hexamethylene, but it is not limited thereto.

In FIG. 1A, (i) may comprise a step of adding an aqueous hydrochloric acid solution to react a diamine with the aqueous hydrochloric acid solution. In FIG. 1A, (ii) may comprise at least one step selected from a precipitation step, a filtration step, a drying step, and a washing step. In FIG. 1B, (iii) may comprise a step of adding triphosgene to react a diamine hydrochloride composition with triphosgene. In FIG. 1B, (iv) may comprise at least one step selected from a degassing step, a filtration step, and a distillation step.

According to an embodiment of the present invention, the content of the benzylmonoamine having a methyl group may be adjusted by introducing the benzylmonoamine having a methyl group to the diamine when the diamine composition is prepared.

In addition, a benzyl isocyanate having a methyl group may be produced in the diisocyanate composition by the introduction of the benzylmonoamine having a methyl group. The content of the benzyl isocyanate having a methyl group produced in the diisocyanate composition may vary with the content of the benzylmonoamine having a methyl group.

For example, if the diamine composition comprises 10 ppm to 2,000 ppm of a benzylmonoamine having a methyl group when it is prepared, the content of a benzyl isocyanate having a methyl group that may be produced in the diisocyanate composition may be controlled in an amount of 5 ppm to 200 ppm. As the content of a benzyl isocyanate having a methyl group is adjusted within the above range, it is possible to enhance the impact resistance and to prevent the occurrence of striae and cloudiness at the same time when the composition is applied to an optical material.

In addition, according to an embodiment of the present invention, the content of a benzyl isocyanate having a methyl group may be adjusted by adding the benzyl isocyanate having a methyl group to the diisocyanate composition. For example, according to an embodiment of the present invention, the content of a benzyl isocyanate having a methyl group may be adjusted by introducing the benzyl isocyanate having a methyl group in the step of obtaining the diamine hydrochloride composition and/or the step of obtaining the diisocyanate composition.

In addition, the benzyl isocyanate having a methyl group may be produced during the process for preparing the diisocyanate composition. For example, it may be produced in the process for preparing a diisocyanate composition during the reaction in the step of obtaining the diamine hydrochloride composition and/or the step of obtaining the diisocyanate composition.

In addition, the benzyl isocyanate having a methyl group may be produced during the process for preparing the diisocyanate composition, and a part thereof may be further added. That is, the amount of the benzyl isocyanate having a methyl group produced during the process for preparing the diisocyanate composition is not sufficient, it may be further added to the composition such that the content thereof is 5 ppm to 200 ppm.

Further, in the preparation process according to an embodiment of the present invention, a diisocyanate, which is mainly used as a raw material for plastic optical lenses, is prepared from a diamine composition through a hydrochloride thereof by way of using an aqueous hydrochloric acid solution instead of hydrogen chloride gas and solid triphosgene instead of phosgene gas while adjusting the reaction conditions. Thus, it is possible to solve the problems that phosgene gas used in the conventional phosgene method is highly toxic and is a substance subject to environmental regulations and that there is a difficulty in storage and management since a separate cooling apparatus is required to store it. It is also possible to solve the problems related to the yield and quality of the product.

In the process for preparing a diisocyanate composition according to an embodiment, the diamine used as a raw material may be xylylenediamine. Alternatively, the diamine may be other diamines used in the production of optical materials. Specifically, it may be at least one selected from the group consisting of orthoxylylenediamine (o-XDA), metaxylylenediamine (m-XDA), paraxylylenediamine (p-XDA), norbornenediamine (NBDA), hydrogenated xylylenediamine (H6XDA), and isophoronediamine (IPDA).

Preparation of a Diamine Hydrochloride Composition

First, a diamine composition is reacted with an aqueous hydrochloric acid solution to obtain a diamine hydrochloride composition (step 1).

As described above, the diamine composition is a composition in which the content of a benzylmonoamine having a methyl group in the composition is 10 ppm to 2,000 ppm.

In addition, after the reaction of the diamine and the aqueous hydrochloric acid solution, a first organic solvent may be further added to obtain the diamine hydrochloride composition in a solid phase.

The following Reaction Scheme 1 shows an example of the reaction in this step.

[Reaction Scheme 1]

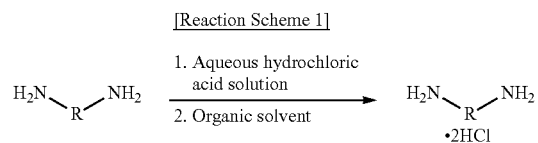

In the above scheme, R comprises an aromatic ring, an aliphatic ring, an aliphatic chain, and the like. As a specific example, R may be xylylene, norbornene, hydrogenated xylylene, isophorone, or hexamethylene, but it is not limited thereto.

In the conventional method in which hydrogen chloride gas is used, a hydrochloride is produced as fine particles upon the reaction at atmospheric pressure, so that the agitation inside the reactor is not smoothly carried out. Thus, an additional process of raising the pressure to increase the internal temperature of the reactor is required, and there is a problem that the yield of the final product is low as well.

According to the above embodiment, however, since an aqueous hydrochloric acid solution is used, it is possible to solve the problem involved in the prior art in which hydrogen chloride gas is used. Specifically, when an aqueous hydrochloric acid solution is used, the product obtained through the reaction is in a solid form rather than a slurry form, so that the yield is high. The reaction can be carried out even at atmospheric pressure, so that a separate apparatus or process for rapid cooling is not required.

The concentration of the aqueous hydrochloric acid solution may be 5% by weight to 50% by weight. Within the above concentration range, it is possible to minimize the dissolution of the hydrochloride in the aqueous hydrochloric acid solution, thereby enhancing the final yield, and to improve the handling convenience.

Specifically, the concentration of the aqueous hydrochloric acid solution may be 10% by weight to 45% by weight, 20% by weight to 45% by weight, or 30% by weight to 40% by weight. More specifically, the aqueous hydrochloric acid solution may have a concentration of 20% by weight to 45% by weight.

The diamine composition and the aqueous hydrochloric acid solution may be introduced to the reaction at an equivalent ratio of 1:2 to 5. If the equivalent ratio is within the above range, it is possible to reduce the unreacted materials and to prevent a decrease in the yield caused by dissolution as water is generated. Specifically, the diamine composition and the aqueous hydrochloric acid solution may be introduced to the reaction at an equivalent ratio of 1:2 to 2.5.

In addition, the amount of the aqueous hydrochloric acid solution introduced may be adjusted at a molar ratio relative to the amount of the diamine introduced. For example, the aqueous hydrochloric acid solution may be introduced such that the amount of HCl is 2 moles or more, 2.02 moles or more, 2.05 moles or more, 2.1 moles or more, or 2.2 moles or more, per 1 mole of the diamine in the diamine composition. In addition, the aqueous hydrochloric acid solution may be introduced such that the amount of HCl is 3 moles or less, 2.7 moles or less, 2.5 moles or less, 2.4 moles or less, 2.35 moles or less, or 2.25 moles or less, per 1 mole of the diamine. Specifically, the aqueous hydrochloric acid solution may be introduced such that the amount of HCl is 2.02 moles to 2.50 moles per 1 mole of the diamine. Within the above range, it may be more advantageous for preventing that a part of the diamine remains as it fails to react with the aqueous hydrochloric acid solution and that the free amine groups react with a diisocyanate in the subsequent reaction to form urea. At the same time, it may be more advantageous for preventing that the remaining chlorine ions caused by the excess aqueous hydrochloric acid solution increase the concentration of chlorine in the subsequent phosgenation reaction to produce impurities.

The introduction of the diamine composition and the aqueous hydrochloric acid solution may be carried out while the internal temperature of the reactor is maintained to be constant.

When the diamine composition and the hydrochloric acid aqueous solution are introduced, the internal temperature of the reactor may be in the range of 20° C. to 100° C. Within the above temperature range, it is possible to prevent the temperature from being raised above the boiling point, which is not suitable for the reaction, or the temperature from being lowered too much, whereby the reaction efficiency is reduced.

Specifically, when the diamine composition and the hydrochloric acid aqueous solution are introduced, the internal temperature of the reactor may be 20° C. to 60° C., 20° C. to less than 60° C., 20° C. to 50° C., or 20° C. to 40° C.

More specifically, the diamine composition and the aqueous hydrochloric acid solution may be introduced to the reaction at an equivalent ratio of 1:2 to 5 at a temperature of 20° C. to 40° C.

In the conventional hydrochloride method, a large amount of heat is generated in the reaction, which requires rapid cooling through a separate cooler, whereas the reaction materials are introduced while a low temperature is maintained according to the above embodiment, which does not require a separate cooler.

The introduction of the diamine composition and the aqueous hydrochloric acid solution may be carried out, for example, in a sequence in which the hydrochloric acid aqueous solution may be first introduced to the reactor and the diamine composition may then be slowly introduced to the reactor. The introduction of the diamine composition and/or the aqueous hydrochloric acid solution may be carried out for 30 minutes to 1 hour.

When the introduction of the diamine composition and the hydrochloric acid aqueous solution is completed, the internal temperature of the reactor may be lowered to 0° C. to 20° C., 0° C. to 10° C., or 10° C. to 20° C.

The reaction between the diamine composition and the aqueous hydrochloric acid solution may be carried out at atmospheric pressure for, for example, 30 minutes to 2 hours with stirring.

As a result of the reaction between the diamine composition and the aqueous hydrochloric acid solution, a diamine hydrochloride composition in an aqueous solution form may be obtained as the reaction resultant.

According to an embodiment of the present invention, the process may further comprise treating the diamine hydrochloride composition after the diamine hydrochloride composition is obtained.

For example, the step of treating the diamine hydrochloride composition may comprise at least one of precipitating the diamine hydrochloride composition, filtering the diamine hydrochloride composition, drying the diamine hydrochloride composition, and washing the diamine hydrochloride composition.

Specifically, a first organic solvent may be introduced to the reaction resultant to precipitate a solid diamine hydrochloride composition. That is, the first organic solvent may induce the precipitation of a solid diamine hydrochloride composition through crystallization. More specifically, the first organic solvent may be introduced to the reaction resultant, which is cooled and further stirred to carry out the reaction.

The first organic solvent may be at least one selected from the group consisting of diethyl ether, diisopropyl ether, dioxane, tetrahydrofuran, methanol, ethanol, dimethyl sulfoxide, dimethylformamide, acetonitrile, acetone, trichloroethylene, tetrachloroethane, trichloroethanol, n-butanol, isobutanol, methyl ethyl ketone, methyl butyl ketone, isopropanol, hexane, chloroform, and methyl acetate.

The amount (weight) of the first organic solvent introduced may be 1 to 5 times the weight of the diamine composition. If the introduced amount is within the above range, it is possible to prevent the use of excessive organic solvents while the yield of the final hydrochloride is high. Specifically, the first organic solvent may be introduced to the reaction in an amount of 1 to 2 times, or 1 to 1.5 times, the weight of the diamine composition.

After the first organic solvent is introduced, the cooling temperature may be −10° C. to 10° C. or −5° C. to 5° C. In addition, the additional reaction time after the cooling may be 30 minutes to 2 hours or 30 minutes to 1 hour.

According to a specific example, the reaction in this step may be sequentially comprise the steps of (1a) introducing the aqueous hydrochloric acid solution to a first reactor; (1b) introducing the diamine composition to the first reactor and stirring them; and (1c) introducing the first organic solvent to the first reactor and stirring them.

More specifically, the reaction in this step may further comprise cooling the inside of the reactor to a temperature of 0° C. to 10° C. after the introduction of the diamine composition and before stirring in step (1b); and cooling the inside of the reactor to a temperature of −5° C. to 5° C. after the introduction of the first organic solvent and before stirring in step (1c).

Meanwhile, according to an embodiment of the present invention, the benzylmonoamine having a methyl group contained in the diamine composition may react with an aqueous hydrochloric acid solution. Through this reaction, the diamine hydrochloride composition may comprise a benzylmonoamine hydrochloride having a methyl group.

After the first organic solvent is introduced, separation, filtration, washing, and drying may be further carried out. For example, after the first organic solvent is introduced, the aqueous layer may be separated, filtered, washed, and dried to obtain a solid diamine hydrochloride composition. The washing may be carried out one or more times using, for example, a solvent having a polarity index of 5.7 or less. In addition, the drying may be carried out using vacuum drying. For example, it may be carried out at a temperature of 40° C. to 90° C. and a pressure of 2.0 torr or less.

As a result, the impurities generated in the step of obtaining the diamine hydrochloride composition may be removed together with the first organic solvent. Thus, the process may further comprise removing the impurities generated in the step of obtaining the diamine hydrochloride composition together with the first organic solvent. Impurities are generated in the reaction for preparing the diamine hydrochloride composition and are contained in the first organic solvent. Such impurities may be removed by the step of removing the first organic solvent, whereby the purity of the product may be increased.

According to the above process, a diamine is reacted with an aqueous hydrochloric acid solution, which is then subjected to additional treatment such as precipitation, filtration, drying, and washing, whereby a solid diamine hydrochloride composition can be obtained with high purity. In contrast, in the conventional process in which a diamine is reacted with hydrogen chloride gas in an organic solvent, a slurry of a diamine hydrochloride is obtained, which is not readily purified.

The yield of the diamine hydrochloride composition thus obtained may be 50% or more, 65% or more, 80% or more, 85% or more, or 90% or more, specifically 85% to 95% or 88% to 92%.

Meanwhile, the organic layer can be separated from the reactant and recycled as an organic solvent. Thus, the recovery rate of the first organic solvent may be 80% or more, 85% or more, or 90% or more, specifically 80% to 95% or 80% to 82%.

Diamine Hydrochloride Composition

According to the embodiment, since a diamine composition whose b* value according to the CIE color coordinate is adjusted is used as a starting material, the b* value of the diamine hydrochloride composition obtained therefrom may also be adjusted. For example, the diamine hydrochloride composition prepared by the process according to the above embodiment has a b* value according to the CIE color coordinate of 1.5 or less, 1.2 or less, 1.0 or less, or 0.8 or less, when dissolved in water at a concentration of 8% by weight. Specifically, the b* value according to the CIE color coordinate may be 0.01 to 1.2, 0.1 to 1.2, 0.1 to 1.0, 0.1 to 0.8, or 0.2 to 1.0.

In addition, in order to adjust the b* value of the diamine hydrochloride composition, an aqueous hydrochloric acid solution having a content of Fe ions at a certain level or less may be used as a raw material. For example, the content of Fe ions in the aqueous hydrochloric acid solution used for preparing the diamine hydrochloride composition may be 0.5 ppm or less. Specifically, the content of Fe ions in the aqueous hydrochloric acid solution may be 0.3 ppm or less or 0.2 ppm or less. More specifically, the content of Fe ions in the aqueous hydrochloric acid solution may be 0.001 ppm to 0.5 ppm or 0.1 ppm to 0.3 ppm.

Alternatively, the b* value according to the CIE color coordinate of the diamine hydrochloride composition may be adjusted by washing it with a solvent having a polarity index of 5.7 or less. In such event, the solvent having a polarity index of 5.7 or less may comprise dichloromethane, and other solvents may be used. In addition, the temperature of the solvent having a polarity of 5.7 or less may be 5° C. or lower, for example, 0° C. to 5° C.

That is, the process according to the embodiment may further comprise washing the diamine hydrochloride composition with a solvent having a polarity of 5.7 or less at 5° C. or lower.

In addition, the process according to the embodiment may further comprise measuring the b* value according to the CIE color coordinate of the diamine hydrochloride composition. If the b* value thus measured is greater than 1.5, the b* value of the diamine hydrochloride composition may be adjusted by repeating the above washing. As a result, the b* value according to the CIE color coordinate of the diamine hydrochloride composition may be adjusted to 1.5 or less when dissolved in water at a concentration of 8% by weight.

The diamine hydrochloride composition obtained by the above process mainly comprises a diamine hydrochloride, and the content of the diamine hydrochloride may be 85% by weight to 99.9% by weight based on the total weight of the composition. In such event, the diamine hydrochloride may contain two of HCl bonded to the two terminal amine groups of the diamine.

In addition, the diamine hydrochloride composition may comprise Fe ions, and the content of Fe ions may be 10 ppm or less based on the total weight of the diamine hydrochloride composition.

In addition, the content of water in the diamine hydrochloride composition may be 5% by weight or less, 1% by weight or less, 0.1% by weight or less, or 0.01% by weight or less.

Preparation of a Diisocyanate Composition

The diamine hydrochloride composition is reacted with triphosgene to obtain a diisocyanate composition (step 2). Specifically, a diisocyanate composition is obtained from the diamine hydrochloride composition by the phosgenation reaction.

The step of obtaining a diisocyanate composition may comprise reacting the diamine hydrochloride composition, treated by the process comprising at least one of precipitation, filtration, drying, and/or washing, with triphosgene.

In such event, the reaction of the diamine hydrochloride composition with triphosgene may be carried out in a second organic solvent.

The following Reaction Scheme 2 shows an example of the reaction in this step.

[Reaction Scheme 2]

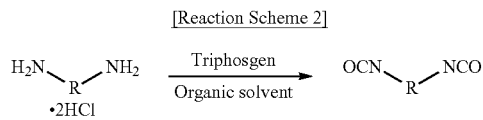

In the above scheme, R comprises an aromatic ring, an aliphatic ring, an aliphatic chain, and the like. As a specific example, R may be xylylene, norbornene, hydrogenated xylylene, isophorone, or hexamethylene, but it is not limited thereto.

Specifically, the diamine hydrochloride composition prepared above is introduced to a second organic solvent, reacted with triphosgene (BTMC, bis(trichloromethyl)carbonate), and then purified to obtain a diisocyanate composition.

According to an embodiment of the present invention, the benzylmonoamine hydrochloride having a methyl group produced in step 1 may be reacted with triphosgene to produce a benzyl isocyanate having a methyl group.

In addition, in the diamine composition, the content of the benzyl isocyanate having a methyl group produced in the diisocyanate composition may vary with the introduced amount of the benzylmonoamine having a methyl group.

The ratio of the production of the benzyl isocyanate having a methyl group to the content of the benzylmonoamine having a methyl group may be 0.05 to 0.9. Specifically, the ratio of production of the benzyl isocyanate having a methyl group to the content of the benzylmonoamine having a methyl group may be 0.06 to 0.8, 0.08 to 0.7, 0.09 to 0.6, 0.09 to 0.25, 0.08 to 0.2, 0.05 to 0.1, or 0.1 to 0.6.

For example, if the content of the benzylmonoamine having a methyl group is 10 ppm to 2,000 ppm, the benzyl isocyanate having a methyl group may be contained in the diisocyanate composition in an amount of 5 ppm to 200 ppm.

Alternatively, if the content of the benzylmonoamine having a methyl group is 10 ppm to 1,000 ppm, the benzyl isocyanate having a methyl group may be contained in the diisocyanate composition in an amount of 5 ppm to 150 ppm.

Alternatively, if the content of the benzylmonoamine having a methyl group is 100 ppm to 2,000 ppm, the benzyl isocyanate having a methyl group may be contained in the diisocyanate composition in an amount of 25 ppm to 200 ppm.

Alternatively, if the content of the benzylmonoamine having a methyl group is 500 ppm to 2,000 ppm, the benzyl isocyanate having a methyl group may be contained in the diisocyanate composition in an amount of 30 ppm to 200 ppm.

In addition, if necessary, the benzyl isocyanate having a methyl group may be contained in the diisocyanate composition in an amount of 5 ppm to 200 ppm.

Meanwhile, the second organic solvent may be at least one selected from the group consisting of benzene, toluene, ethylbenzene, chlorobenzene, monochlorobenzene, 1,2-dichlorobenzene, dichloromethane, 1-chloro-n-butane, 1-chloro-n-pentane, 1-chloro-n-hexane, chloroform, carbon tetrachloride, n-pentane, n-hexane, n-heptane, n-octane, cyclohexane, cyclopentane, cyclooctane, and methylcyclohexane.

The amount (weight) of the second organic solvent introduced may be 1 to 5 times the weight of the diamine hydrochloride composition. If the introduced amount is within the above range, it is possible to prevent the use of excessive organic solvents while the yield of the final diisocyanate is high. Specifically, the second organic solvent may be introduced to the reaction in an amount of 2 to 5 times, or 3 to 5 times, the weight of the diamine hydrochloride composition.

The reaction temperature of the diamine hydrochloride composition and triphosgene may be 110° C. to 160° C. or 115° C. to 160° C. If the reaction temperature is within the above range, specifically 110° C. or 115° C. or higher, the reaction between the diamine hydrochloride and triphosgene can be more smoothly carried out, and it may be advantageous for increasing the yield and shortening the reaction time. If it is 160° C. or less, it is possible to suppress the generation of impurities such as tar when the final diisocyanate is produced. Specifically, the reaction temperature of the diamine hydrochloride composition and triphosgene may be 115° C. to 160° C., 115° C. to 140° C., 115° C. to 130° C., 115° C. to 120° C., 130° C. to 160° C., or 120° C. to 150° C.

The reaction of the diamine hydrochloride composition with triphosgene may be carried out for 5 hours to 100 hours. If the reaction time is within the above range, the reaction time is not excessive, and the production of unreacted materials due to the generation of phosgene can be minimized. Specifically, the reaction of the diamine hydrochloride composition with triphosgene may be carried out for 15 hours to 40 hours, 20 hours to 35 hours, or 24 hours to 30 hours.

As a specific example, the reaction of the diamine hydrochloride composition with triphosgene may be carried out at a temperature of 110° C. to 160° C. or 115° C. to 160° C. for 5 hours to 100 hours.

The diamine hydrochloride composition and triphosgene may be introduced to the reaction at an equivalent ratio of 1:1 to 5. When the equivalent ratio is within the above range, the reaction efficiency is high, and it is possible to prevent an increase in the reaction time due to an excessive introduction. Specifically, the diamine hydrochloride composition and triphosgene may be introduced to the reaction at an equivalent ratio of 1:1.5 to 4 or 1:2 to 2.5.

Alternatively, the diamine hydrochloride composition and triphosgene may be introduced to the reaction at a molar ratio of 1:0.65 to 1. Specifically, the diamine hydrochloride composition and triphosgene may be introduced to the reaction at a molar ratio of greater than 1:0.70 to less than 0.95 or 1:0.73 to 0.90. When the molar ratio is within the above range, the reaction efficiency is high, and it is advantageous for preventing an increase in reaction time due to an excessive introduction.

The reaction of the diamine hydrochloride composition and triphosgene may sequentially comprise mixing the diamine hydrochloride composition with a second organic solvent to obtain a first solution; mixing triphosgene with the second organic solvent to obtain a second solution; and introducing the second solution to the first solution and stirring them. In such event, the introduction of the second solution and stirring may be carried out at a temperature of 110° C. to 160° C. or 115° C. to 160° C. In addition, the introduction of the second solution may be divided into two or more times for a total of 25 hours to 40 hours. In addition, here, the time for each introduction may be 5 hours to 25 hours or 10 hours to 14 hours. In addition, the time for further reaction by stirring after the introduction may be 2 hours to 5 hours or 3 hours to 4 hours.

Alternatively, the reaction of the diamine hydrochloride composition and triphosgene may sequentially comprise (2a) introducing the second organic solvent to a second reactor; (2b) further introducing the diamine hydrochloride composition to the second reactor and stirring them; and (2c) further introducing triphosgene to the second reactor and stirring them.

In addition, the introduction of triphosgene in step (2c) may be carried out by introducing a solution in which triphosgene is dissolved in the same solvent as the second organic solvent to the reactor as divided into two or more times at a temperature of 110° C. to 160° C. or 115° C. to 130° C. for a total of 25 hours to 40 hours.

In such event, the time for each introduction of triphosgene may be 5 hours to 25 hours or 10 hours to 14 hours.

In addition, the time for further reaction by stirring after the introduction of triphosgene may be 2 hours to 5 hours or 3 hours to 4 hours.

Upon the reaction, the reactant may be cooled at a temperature of 90° C. to 110° C.

The reaction resultant obtained through the reaction may be further subjected to separation, degassing, filtration, and distillation.

For example, after the reaction, the reaction resultant may be subjected to degassing at 80° C. to 150° C. with the bubbling of nitrogen gas. In addition, after the degassing, it may be cooled to 10° C. to 30° C., and solids may be filtered off.

The diisocyanate composition may be obtained by distillation after the phosgenation reaction of the diamine hydrochloride composition.

The distillation may comprise distillation to remove the second organic solvent. For example, after the reaction, the reaction resultant may be distilled at 40° C. to 60° C. for 2 hours to 8 hours to remove the second organic solvent. The pressure during the distillation may be 2.0 torr or less, 1.0 torr or less, 0.5 torr or less, or 0.1 torr or less. In addition, the second organic solvent may be recovered and recycled through the distillation.

In addition, the distillation may comprise distilling the diisocyanate. For example, the distillation may comprise distillation of a diisocyanate at 100° C. to 130° C. If the distillation temperature is within the above range, it is more advantageous for preventing a deterioration in the physical properties of the final optical lens such as stria, cloudiness, and yellowing by effectively removing hydrolyzable chlorine compounds generated at high temperatures such as chloromethylbenzyl isocyanate (CBI) and 1,3-bis(chloromethyl)benzene. Specifically, the distillation may be carried out by setting the bottom temperature of the distiller to 100° C. to 130° C. For example, the distillation may be carried out by setting the reboiler temperature to 100° C. to 130° C.

In addition, the pressure during the distillation may be 2.0 torr or less, 1.0 torr or less, 0.5 torr or less, or 0.1 torr or less. Specifically, the distillation may comprise distillation of a diisocyanate at a temperature of 100° C. to 130° C. and a pressure of 2 torr or less.

In addition, the time for distillation of a diisocyanate may be 1 hour or longer, 2 hours or longer, or 3 hours or longer, and may be 10 hours or shorter or 5 hours or shorter. Specifically, the distillation of a diisocyanate may be carried out for 2 hours to 10 hours.

Alternatively, according to an embodiment of the present invention, the process may further comprise distilling the reaction resultant after the reaction in step 2, and the distillation may comprise first distillation and second distillation.

For example, the step of obtaining the diisocyanate composition further comprises distilling the reaction resultant obtained by reacting the diamine hydrochloride composition, specifically the treated diamine hydrochloride composition, with triphosgene. The distillation may comprise first distillation at 40° C. to 60° C. for 2 hours to 8 hours and second distillation at 100° C. to 120° C. for 2 hours to 10 hours. The first distillation and/or the second distillation may be carried out at 0.5 Torr or less.

The organic solvent may be recovered and recycled through the first distillation, and a final diisocyanate may be obtained through the second distillation.

The yield of the distillation of the diisocyanate thus obtained may be 80% or more, specifically 85% or more, 87% or more, or 90% or more. In such event, the distillation yield may be calculated by measuring the amount of the diisocyanate composition upon the distillation relative to the theoretical amount of the diisocyanate composition produced from the amounts of the diamine hydrochloride composition introduced to the phosgenation reaction.

According to the process of the above embodiment, the reaction temperature range of the diamine hydrochloride composition and triphosgene is controlled, whereby the crude diisocyanate composition before purification may contain very little impurities. Specifically, the diisocyanate composition may contain 99.0% by weight or more of the diisocyanate before the distillation of a diisocyanate. In addition, the diisocyanate composition may contain 99.9% by weight or more of the diisocyanate after the distillation of a diisocyanate.

In addition, the content of aromatic compounds having a halogen group in the diisocyanate composition may be 1,000 ppm or less.

In addition, the yield of the diisocyanate composition finally obtained may be 80% or more, 85% or more, 88% or more, or 90% or more.

[Diisocyanate Composition]

According to an embodiment, the content of the benzyl isocyanate having a methyl group in the diisocyanate composition may be 5 ppm to 200 ppm.

According to an embodiment of the present invention, if an optical material is prepared while the content of a benzyl isocyanate having a methyl group in the diisocyanate composition is adjusted to the optimum range through the content of the benzylmonoamine having a methyl group, it is possible to further enhance the physical properties of the optical material.

In addition, the benzyl isocyanate having a methyl group may be produced during the process for preparing the diisocyanate composition.

In addition, the benzyl isocyanate having a methyl group may be produced during the process for preparing the diisocyanate composition, and a part thereof may be intentionally added. That is, the benzyl isocyanate having a methyl group may be produced during the process for preparing the diisocyanate composition. If the amount thus produced is not sufficient, it may be intentionally added to the composition such that the content thereof is 5 ppm to 200 ppm in the composition.

The benzyl isocyanate having a methyl group may comprise a benzyl isocyanate having a methyl group with a specific aromatic structure. Specifically, it may comprise at least one selected from the group consisting of 2-methylbenzyl isocyanate substituted with a methyl group at the ortho (o) position, 3-methylbenzyl isocyanate substituted with a methyl group at the meta (m) position, and 4-methylbenzyl isocyanate substituted with a methyl group at the para (p) position.

According to an embodiment of the present invention, the benzyl isocyanate having a methyl group may comprise at least one selected from the group consisting of 3-methylbenzyl isocyanate substituted with a methyl group at the meta (m) position and 4-methylbenzyl isocyanate substituted with a methyl group at the para (p) position.

According to an embodiment of the present invention, a benzyl isocyanate having a methyl group, in particular, 3-methylbenzyl isocyanate or 4-methylbenzyl isocyanate is employed in a specific amount. In such event, since it has one isocyanate functional group, it may stop the crosslinking reaction in the reaction for producing a polythiourethane, thereby promoting the enhancement in the flexibility of the polythiourethane. Thus, it is possible to prevent the occurrence of striae and cloudiness in an optical material, for example, an optical lens and enhancing the impact resistance at the same time.

According to still another embodiment of the present invention, the benzyl isocyanate having a methyl group may comprise at least one selected from the group consisting of 3-methylbenzyl isocyanate substituted with a methyl group at the meta (m) position and 2-methylbenzyl isocyanate substituted with a methyl group at the ortho (o) position.

More specifically, the benzyl isocyanate having a methyl group may comprise a compound of the following Formula 2 in which a methyl group is substituted at the meta (m) position.

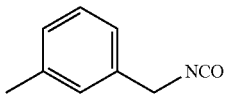

[Formula 2]

According to an embodiment of the present invention, the content of the benzyl isocyanate having a methyl group contained in the composition may be 5 ppm to 200 ppm, 10 ppm to 200 ppm, 20 ppm to 150 ppm, 20 ppm to less than 100 ppm, 100 ppm to 200 ppm, 120 ppm to 200 ppm, 50 ppm to 200 ppm, or 50 ppm to 150 ppm. According to an embodiment of the present invention, the content of the benzyl isocyanate having a methyl group contained in the composition is adjusted within the above range, whereby it is possible to enhance the impact resistance and to prevent the occurrence of striae and cloudiness.

If the content of the benzyl isocyanate having a methyl group is not adjusted, the impact resistance may be deteriorated, or striae and cloudiness may occur even if the impact resistance is maintained. For example, if the content of the benzyl isocyanate having a methyl group is less than 5 ppm, the impact resistance of the optical material using the composition may be deteriorated. On the other hand, if the content of the benzyl isocyanate having a methyl group exceeds 200 ppm, striae or cloudiness may occur even if the impact resistance of the optical material using the composition is enhanced.

Meanwhile, the diisocyanate composition may comprise a diisocyanate in an amount of 90% by weight or more, 95% by weight or more, 99.5% by weight or more, 99.9% by weight or more, 90% by weight to 99.9% by weight, or 99% by weight to less than 100% by weight, based on the total weight of the composition.

The diisocyanate may comprise m-xylylene diisocyanate (m-XDI), p-xylylene diisocyanate (p-XDI), or a mixture thereof.

The diisocyanate composition according to an embodiment may comprise m-xylylene diisocyanate (m-XDI) in an amount of 99% by weight to less than 100% by weight, 99.5% by weight to less than 100% by weight, or 99.7% by weight to less than 100% by weight.

If m-xylylene diisocyanate is contained in the composition in an amount less than the above range, not only the optical characteristics (especially, striae, transmittance, and the like) but also the mechanical properties (such as impact resistance, tensile strength, and the like) of the final product may be impaired due to the nonuniformity in the polymerization reactivity of the composition and in the chemical structure of the cured product. Further, yellowing may occur depending on other components incorporated therein.

According to an embodiment, the composition may comprise the compound of Formula 2 in an amount of 20 ppm to 150 ppm and m-xylylene diisocyanate in an amount of 99.5% by weight to less than 100% by weight based on the total weight of the composition.

In addition, p-xylylene diisocyanate may be contained in an amount of greater than 0% by weight to 0.5% by weight, greater than 0% by weight to 0.3% by weight, greater than 0% by weight to 0.15% by weight, greater than 0% by weight to 0.1% by weight, greater than 0% by weight to 0.05% by weight, greater than 0% by weight to 0.03% by weight, or greater than 0% by weight to 0.01% by weight, based on the total weight of the composition.

If p-xylylene diisocyanate is contained in the composition in an amount exceeding the above content range, the optical characteristics may be impaired as striae occur or the transmittance is lowered due to the nonuniform polymerization caused by differences in the reactivity or due to the crystallization caused by changes in the chemical structure of the polymer.

In addition, the diisocyanate composition may comprise other diisocyanates used in the preparation of optical lenses than m-xylylene diisocyanate and p-xylylene diisocyanate. Specifically, the composition may comprise at least one selected from the group consisting of orthoxylylene diisocyanate (o-XDI), norbornene diisocyanate (NBDI), hydrogenated xylylene diisocyanate (H6XDI), isophorone diisocyanate (IPDI), and hexamethylene diisocyanate (HDI).

In addition, the diisocyanate composition of the present invention may further comprise at least one selected from the group consisting of a benzyl isocyanate having an ethyl group and cyanobenzyl isocyanate.

The at least one selected from the group consisting of a benzyl isocyanate having an ethyl group and cyanobenzyl isocyanate may be employed in an amount of, for example, 0.5% by weight or less, 0.3% by weight or less, 0.1% by weight or less, 0.05% by weight or less, 0.02% by weight or less, or 0.01% by weight or less.

If the at least one selected from the group consisting of a benzyl isocyanate having an ethyl group and cyanobenzyl isocyanate is employed in the composition in an amount exceeding the above content range, it affects the chemical structure of the polymer, resulting in a deterioration in the mechanical properties or the thermal resistant characteristics such as glass transition temperature of the final product. Further, due to the influence of the cyano groups, yellowing may occur at the time of thermal curing for producing a lens or after the production of the lens depending on the external environment, thereby causing serious damage to the long-term reliability of the lens.

Therefore, a product produced from the diisocyanate composition whose composition has been adjusted as described above can satisfy excellent optical characteristics, as well as can achieve excellent mechanical properties. Thus, it can be advantageously used for the production of optical materials, specifically plastic optical lenses.

In addition, the diisocyanate composition prepared as described above may be improved in terms of the color and haze.

In particular, the diisocyanate composition prepared by the process according to the above embodiment may have a b* value according to the CIE color coordinate of 0.01 to 2.0. An optical lens prepared from the diisocyanate composition having a value of b* within the above range may be improved in stria, transmittance, yellow index, and refractive index. Specifically, the b* value according to the CIE color coordinate of the diisocyanate composition may be 0.1 to 2.0, 0.1 to 1.5, 0.1 to 1.2, 0.1 to 1.0, or 0.1 to 0.8.

In addition, the diisocyanate composition may have an APHA (American Public Health Association) color value of 20 or less or 10 or less. Specifically, the diisocyanate composition may have an APHA color value of 1 to 20 or 1 to 10.

In addition, the diisocyanate composition may have a haze of 10% or less, 5% or less, or 3% or less.

In addition, the content of Fe ions in the diisocyanate composition may be 10 ppm or less, 5 ppm or less, or 1 ppm or less. Specifically, the content of Fe ions in the diisocyanate composition may be 0.2 ppm or less.

In order to improve the color and haze, the diisocyanate composition may comprise xylylene diisocyanate or other diisocyanates used in the preparation of optical lenses. Specifically, it may comprise at least one selected from the group consisting of orthoxylylene diisocyanate (o-XDI), metaxylylene diisocyanate (m-XDI), paraxylylene diisocyanate (p-XDI), norbornene diisocyanate (NBDI), hydrogenated xylylene diisocyanate (H6XDI), isophorone diisocyanate (IPDI), and hexamethylene diisocyanate (HDI) in an amount of 90% by weight or more, 95% by weight or more, 99.5% by weight or more, 99.9% by weight or more, or 90% by weight to 99.9% by weight. It may further comprise benzyl isocyanate, methylbenzyl isocyanate, cyanobenzyl isocyanate, and the like in a total content of about 1% by weight or less.

Measurement of the Color and Transparency of a Reaction Solution

The step of obtaining a diisocyanate composition from the diamine hydrochloride composition and triphosgene may comprise (aa) reacting the diamine hydrochloride composition with triphosgene in a reactor to obtain a reaction solution; (ab) measuring the color and transparency of the reaction solution; and (ac) obtaining a diisocyanate composition from the reaction solution.

In the reaction of the diamine hydrochloride composition and triphosgene, the color and transparency of the reaction solution may be measured to adjust the reaction conditions.

For example, in the reaction of metaxylylenediamine hydrochloride and triphosgene to obtain metaxylylene diisocyanate, the reaction solution at the beginning of the reaction may be opaque colorless or white, and the reaction solution at the time when the reaction is ordinarily completed may be transparent or close to transparent in a light brown color.

For example, in the step of measuring the color and transparency of the reaction solution, the reaction solution may have a transparent light brown color.

Specifically, the reaction solution may have an L* value of 45 to 60, an a* value of 3 to 15, and a b* value of 15 to 30 in the CIE-LAB color coordinate. More specifically, the reaction solution may have an L* value of 50 to 55, an a* value of 5 to 10, and a b* value of 20 to 25 in the CIE-LAB color coordinate.

In addition, the reaction solution may have a transmittance of 60% or more, 70% or more, 80% or more, or 90% or more, for light having a wavelength of 550 nm. In addition, the reaction solution may have a haze of 20% or less, 10% or less, 5% or less, or 3% or less. Specifically, the reaction solution may have a transmittance of 70% or more for light having a wavelength of 550 nm and a haze of 10% or less. More specifically, the reaction solution may have a transmittance of 80% or more for light having a wavelength of 550 nm and a haze of 5% or less.

On the other hand, if the reaction of the metaxylylenediamine hydrochloride and triphosgene is not completed, the reaction solution may be opaque or have a precipitate, and the color may be pale, white, or colorless. In addition, if side reactions take place to a significant extent, the reaction solution may be opaque or may have a color other than light brown, for example, a dark brown or dark color.

The reaction of the diamine hydrochloride composition and triphosgene may be carried out simultaneously with the step of measuring the color and transparency of the reaction solution.

That is, while the reaction of the diamine hydrochloride composition and triphosgene is being carried out, the color and transparency of the reaction solution may be measured in real time.

In addition, for more accurate measurement, a part of the reaction solution may be collected to precisely measure the color and transparency thereof. For example, the measurement of the color and transparency of the reaction solution may be carried out by collecting a part of the reaction solution and measuring the color and transparency of the collected reaction solution.

In such event, the reaction equivalent, reaction temperature, or reaction time may be adjusted according to the color and transparency of the reaction solution. For example, the timing for terminating the reaction may be determined according to the color and transparency of the reaction solution. Specifically, the timing for terminating the reaction may come after when the reaction solution turns a transparent light brown color.

As an example, the reactor may have a viewing window, and the measurement of the color and transparency of the reaction solution may be carried out through the viewing window.

The reactor is connected to one or more stages of condensers. Once the gas generated in the reactor has been transferred to the one or more stages of condensers, the second organic solvent present in the gas may be condensed and recycled to the reactor.

The one or more stages of condensers are connected to a first scrubber and a second scrubber. The gas transferred from the reactor to the one or more stages of condensers contains hydrogen chloride gas and phosgene gas, the first scrubber may dissolve the hydrogen chloride gas in water to produce an aqueous solution, and the second scrubber may neutralize the phosgene gas with an aqueous NaOH solution.

In addition, the reactor is connected to one or more stages of distillers. The reaction solution is transferred to the one or more stages of distillers, and the one or more stages of distillers may separate the diisocyanate composition and the second organic solvent from the reaction solution.

The separated second organic solvent may be recycled for the reaction of the diamine hydrochloride composition and triphosgene.

FIG. 2 shows an example of the process equipment for the reaction of a diamine hydrochloride composition and triphosgene.

First, a first tank (T-1) is charged with a second organic solvent and triphosgene, and the temperature is maintained to be constant by refluxing hot water. The inside of a reactor (R-1) is purged with nitrogen, a second organic solvent is introduced thereto with stirring, a diamine hydrochloride composition is slowly introduced thereto, and they are stirred while the internal temperature of the reactor is maintained to be constant.

Thereafter, triphosgene in the second organic solvent is gradually introduced into the reactor (R-1) from the first tank (T-1). The introduction of triphosgene in the second organic solvent is carried out at a time or divided into two or more times. At that time, stirring is performed while the internal temperature of the reactor (R-1) is maintained to be constant. Upon completion of the introduction, an additional reaction is carried out while stirring is performed for a certain period of time. As an example, the color and transparency of the reaction solution are monitored with the naked eyes through a viewing window (G-1) provided in the reactor (R-1). As another example, the color and transparency of the reaction solution are measured with an optical device through the viewing window (G-1) provided in the reactor (R-1). The optical device may include a digital camera, a spectrometer, and optical analysis equipment.

The gas (second organic solvent, hydrogen chloride, phosgene, and the like) present inside the reactor (R-1) is transferred to a first condenser (C-1). In the first condenser (C-1), the second organic solvent is firstly condensed by cooling and recycled to the reactor (R-1), and the remaining gas is transferred to a second condenser (C-2). In the second condenser (C-2), the second organic solvent is secondly condensed by cooling and recycled to the reactor (R-1), and the remaining gas is transferred to a third condenser (C-3). In the third condenser (C-3), the second organic solvent is thirdly condensed by cooling and recycled to the reactor (R-1).

Once the second organic solvent is removed while it passes through the multi-stage condensers as described above, the remaining gas (hydrogen chloride, phosgene, and the like) is transferred to a first scrubber (S-1). In the first scrubber (S-1), hydrogen chloride gas is dissolved in water to obtain an aqueous hydrochloric acid solution and stored in a second tank (T-2), and the remaining gas is transferred to a second scrubber (S-2). In the second scrubber (S-2), phosgene ($COCl_2$) gas may be neutralized with an aqueous sodium hydroxide solution stored in a third tank (T-3) and removed.

The reaction solution obtained from the reactor (R-1) is sequentially transferred to a first distiller (D-1) and a second distiller (D-2). While it undergoes first and second distillation, the diisocyanate composition and the second organic solvent are separated from the reaction solution.

The second organic solvent separated from the reaction solution may be transferred to, and stored in, a solvent recovery apparatus (V-1). Thereafter, it may be recycled for the reaction of the diamine hydrochloride composition and triphosgene.

In addition, the diisocyanate composition separated from the reaction solution may be further subjected to filtration and drying to provide a final product.

[Process for the Preparation of an Optical Material]

The diisocyanate prepared in the above embodiment may be combined with other components to prepare a polymerizable composition for an optical material. That is, the composition for an optical material comprises a diisocyanate composition prepared according to the above embodiment and a thiol or an episulfide. The composition for an optical material may be used to prepare an optical material, specifically an optical lens. For example, the composition for an optical material is mixed and heated and cured in a mold to produce an optical lens. The process for preparing an optical lens or the characteristic thereof described below should be understood as a process for preparing various optical materials or the characteristic thereof that can be implemented using the diisocyanate composition according to the embodiment in addition to an optical lens.

The process for preparing an optical material according to still another embodiment comprises reacting a diamine composition with an aqueous hydrochloric acid solution to obtain a diamine hydrochloride composition; reacting the diamine hydrochloride composition with triphosgene to obtain a diisocyanate composition; and mixing the diisocyanate composition with a thiol or an episulfide and polymerizing and curing the resultant in a mold, wherein the diamine composition comprises a diamine; and a benzyl-monoamine having a methyl group in an amount of 10 ppm to 2,000 ppm.

The process for preparing an optical material according to still another embodiment comprises obtaining a diamine hydrochloride composition from a diamine composition; obtaining a diisocyanate composition from the diamine hydrochloride composition through a phosgenation reaction; and mixing the diisocyanate composition with a thiol or an episulfide and polymerizing and curing the resultant in a mold, wherein the diamine composition has a b* value according to the CIE color coordinate of 0.01 to 3.0.

In the above preparation process, the respective components and contents of the diamine hydrochloride composition and the diisocyanate composition and the preparation process thereof are as described above.

In addition, the diamine is xylylenediamine, and the diisocyanate composition may comprise xylylene diisocyanate.

The thiol may be a polythiol containing two or more SH groups. It may have an aliphatic, alicyclic, or aromatic skeleton. The episulfide may have two or more thioepoxy groups. It may have an aliphatic, alicyclic, or aromatic skeleton.

Specific examples of the thiol include bis(2-mercaptoethyl) sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropanyl)sulfide, bis(2,3-dimercaptopropanyl)disulfide, 1,2-bis(2-mercaptoethylthio)-3-mercaptopropane, 1,2-bis(2-(2-mercaptoethylthio)-3-mercaptopropylthio)ethane, bis(2-(2-mercaptoethylthio)-3-mercaptopropyl)sulfide, bis(2-(2-mercaptoethylthio)-3-mercaptopropyl)disulfide, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R, 11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaethritol tetrakis(2-mercaptoacetate), bispentaerythritol-ether-hexakis(3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis(mercaptodimethylthio)ethyl)-1,3-dithiane, 2,5-bismercaptomethyl-1,4-dithiane, bis(mercaptomethyl)-3,6,9-trithiaundecan-1,11-dithiol.

For example, the thiol may be 2-(2-mercaptoethylthio)propane-1,3-dithiol, 2,3-bis(2-mercaptoethylthio)propane-1-thiol, 2-(2,3-bis(2-mercaptoethylthio)propylthio)ethanethiol, 1,2-bis(2-mercaptoethylthio)-3-mercaptopropane, 1,2-bis(2-(2-mercaptoethylthio)-3-mercaptopropylthio)-ethane, bis(2-(2-mercaptoethylthio)-3-mercaptopropyl) sulfide, 2-(2-mercaptoethylthio)-3-2-mercapto-3-[3-mercapto-2-(2- mercaptoethylthio)-propylthio]propylthio-propane-1-thiol, 2,2'-thiodiethanethiol, 4,14-bis(mercaptomethyl)-3,6,9,12,15-pentathiahectadecane-1,17-dithiol, 2-(2-mercaptoethylthio)-3-[4-(1-{4-[3-mercapto-2-(2-mercaptoethylthio)-propoxy]-phenyl}-1-methylethyl)-phenoxy]-propane-1-thiol, pentaerythritol tetrakis(3-mercaptopropionate), pentaerythritol mercaptoacetate, trimethanolpropanetrismercaptopropionate, glycerol trimercaptopropionate, dipentaerythritol hexamercaptopropionate, or 2,5-bismercaptomethyl-1,4-dithiane.

The thiol may be any one or two or more of the exemplary compounds, but it is not limited thereto.

In addition, specific examples of the episulfide include bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, 1-(β-epithiopropylthio)-2-[[2-(2-β-epithiopropylthioethyl)thioethyl]thio]ethane, tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl)thiomethyl]-3,7-dithianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, 1,11-bis(β-epithiopropylthio)-4,7-bis(β-epithiopropylthiomethyl)-3,6,9-trithiaundecane, 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl]sulfide, 2,5-bis(β-epithiopropylthiomethyl)-1,4-dithiane, 2,5-bis(β-epithiopropylthioethylthiomethyl)-1,4-dithiane, 1,3-bis(β-epithiopropylthio)benzene, 1,4-bis(β-epithiopropylthio)benzene, 1,3-bis(β-epithiopropylthiomethyl)benzene, 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, and 4,4'-bis(β-epithiopropylthio)biphenyl.

The episulfide may be any one or two or more of the exemplary compounds, but it is not limited thereto. In addition, the episulfide may be a compound in which at least one of the hydrogens of its thioepoxy group is substituted with a methyl group.

The polymerizable composition for an optical material may comprise the diisocyanate composition and the thiol or episulfide in a mixed state or in a separated state. That is, in the composition, they may be in a state of being compounded in contact with each other or separated from each other so as not to contact each other.

The polymerizable composition for an optical material may comprise the thiol or episulfide and the diisocyanate composition at a weight ratio of 2:8 to 8:2, 3:7 to 7:3, or 4:6 to 6:4.

A catalyst, a chain extender, a crosslinking agent, an ultraviolet stabilizer, an antioxidant, an anti-coloring agent, a dye, a filler, a release agent, and the like may be further added depending on the purpose when the composition for an optical material and an optical lens are prepared.

The thiol or episulfide is mixed with a diisocyanate composition and other additives, which is defoamed, injected into a mold, and gradually polymerized while the temperature is gradually elevated from low to high temperatures. The resin is cured by heating to prepare an optical lens.

The polymerization temperature may be, for example, 20° C. to 150° C., particularly 25° C. to 120° C. In addition, a reaction catalyst, which is conventionally used in the production of polythiourethane, may be employed in order to control the reaction rate. Specific examples of the reaction catalyst are as exemplified above.

In addition, if required, the optical lens thus prepared may be subjected to physical or chemical treatment such as anti-reflection coating, hardness, enhancements in abrasion resistance and chemical resistance, anti-fogging, surface polishing, antistatic treatment, hard coat treatment, anti-reflection treatment, and dyeing treatment.

[Optical Material]

The optical material according to an embodiment of the present invention comprises a polythiourethane polymerized from a diisocyanate composition and a thiol or an episulfide, wherein the content of a benzyl isocyanate having a methyl group in the diisocyanate composition is 5 ppm to 200 ppm.

The optical material is not only excellent in transparency, refractive index, and yellow index, but also capable of enhancing the impact resistance and preventing striae and cloudiness.

For example, the optical material may have a refractive index of 1.55 or more or 1.6 or more, specifically a refractive index of 1.55 to 1.77 or 1.6 to 1.7. In addition, the optical material may have an Abbe number of 30 to 50, specifically 30 to 45 or 31 to 40. In addition, the optical material may have a light transmittance of 80% or more, 85% or more, or 87% or more, which may be a total light transmittance. In addition, the optical material may have a yellow index (Y.I.) of 30 or less, 25 or less, 22 or less, or 20 or less, for example, 1 to 25, 10 to 22, or 10 to 20. Specifically, the optical material may have a transmittance of 85% or more and a yellow index of 22 or less.

In addition, the optical material may have excellent impact resistance energy within an appropriate range. The impact resistance energy may be measured as the potential energy of a weight that breaks a specimen prepared in the form of a plate having a diameter of 80 mm and a thickness of 1.2 mm when steel balls having different weights are fallen thereto in a sequence from a light ball to a heavy ball at a height of 127 cm at a temperature of 20° C. according to the test standards of the US FDA. Specifically, steel balls each having a weight of 16 g, 32 g, 65 g, 100 g, 200 g, or 300 g are used in the ball dropping test at various heights to measure the potential energy when an optical material, specifically an optical lens, is broken. For example, the potential energy (Ep) is 0.2 (J) (Ep=mgh=0.016×9.8×1.27=0.2 (J)) for 16 g and 127 cm according to the FDA standard. If a specimen passes the ball dropping test of a steel ball of 16 g, the potential energy (Ep) is then calculated using a steel ball of 32 g. If the specimen passes this test, steel balls each having a weight of 65 g, 100 g, 200 g, or 300 g are sequentially used to measure the potential energy when the specimen is finally broken.

The optical material according to an embodiment of the present invention has an excellent impact resistance energy (E) as measured by the above method, which is 0.3 J to 3.0 J, 0.4 J to 3.0 J, 0.4 J to 2.5 J, 0.6 J to 3.0 J, 0.6 J to 2.8 J, 0.8 J to 2.8 J, or 0.8 J to 2.5 J.

Thus, a diisocyanate composition comprising a specific content of a benzyl isocyanate having a methyl group is used to prepared an optical material, thereby improving the optical characteristics by preventing the occurrence of yellowing, striae, and cloudiness and enhancing the mechanical properties such as impact resistance at the same time. It can be advantageously used to prepare high-quality eyeglass lenses, camera lenses, and the like.

MODE FOR CARRYING OUT THE INVENTION

Hereinafter, more specific embodiments are illustrated, but the present invention is not limited thereto.

Example 1-1

Step 1: Preparation of a Diamine Hydrochloride Composition 3-methylbenzylamine was added to 600 g (4.4 moles) of metaxylylenediamine (m-XDA) to prepare a diamine composition in which the concentration of 3-methylbenzylamine in the diamine composition was adjusted to 10 ppm.

A 5-liter, 4-neck reactor was charged with 1009.4 g (9.46 moles) of an aqueous solution of 35% hydrochloric acid, followed by lowering the internal temperature of the reactor to 15° C. with stirring. While the temperature of the reactor was maintained at lower than 60° C., the diamine composition was introduced for 1 hour. Upon completion of the introduction, the internal temperature of the reactor was lowered to 10° C., and it was stirred for 1 hour. Thereafter, 1,320 g of tetrahydrofuran as an organic solvent was introduced, and the internal temperature of the reactor was lowered to −5° C., followed by stirring for 1 hour. Upon completion of the reaction, it was subjected to vacuum filtration using a filter, and the filtered tetrahydrofuran was recovered for reuse. The recovery rate of the tetrahydrofuran was 82%. Upon completion of the vacuum filtration, a metaxylylenediamine (m-XDA) hydrochloride composition was obtained. In order to remove the residual organic solvent and water, drying was performed under the conditions of a reactor external temperature of 90° C. and a vacuum pump of 0.1 Torr to obtain a final metaxylylenediamine (m-XDA) hydrochloride composition.

Step 2: Preparation of a Diisocyanate Composition

Reactor A was charged with 800 g of the diamine hydrochloride composition prepared above and 3,550 g of orthodichlorobenzene (ODCB), followed by elevating the internal temperature of the reactor to about 125° C. with stirring. Reactor B was charged with 950 g of triphosgene (BTMC) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. It was cooled to 10° C., and the remaining solids were filtered using celite. Thereafter, the organic solvent (ODCB) was removed, and m-XDI was purified by distillation under the following distillation conditions. The removal of the organic solvent (first distillation) was carried out for 8 hours at a pressure of 0.5 torr or less and a temperature of 60° C. The distillation of m-XDI (second distillation) was carried out for 10 hours at a pressure of 0.1 torr or less and a temperature of 120° C., to thereby obtain a m-XDI composition.

Preparation of an Optical Material 49.3 parts by weight of 4,8-bis(mercaptomethyl)-3,6,9-trithiaundecane-1,11-dithiol, 50.7 parts by weight of the m-XDI composition prepared above, 0.01 part by weight of dibutyltin dichloride, and 0.1 part by weight of a phosphate ester release agent (ZELEC® UN Stepan) were homogeneously mixed, which was defoamed at 600 Pa for 1 hour, filtered through a Teflon filter of 3 μm, and injected into a mold made of a glass mold and a tape. The mold was maintained at 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens (or an optical material).

Examples 1-2 to 1-5

A m-XDI composition and an optical lens were obtained in the same manner as in Example 1-1, except that the concentration of 3-methylbenzyl isocyanate introduced was adjusted as shown in Table 1 below.

Comparative Examples 1-1 to 1-7

A m-XDI composition and an optical lens were obtained in the same manner as in Example 1-1, except that the concentration of 3-methylbenzyl isocyanate introduced was adjusted as shown in Table 1 below.

<Evaluation Method>

The Examples and the Comparative Examples were evaluated as follows.

(1) Haze (Cloudiness)

The cured lens was irradiated to a projector in a darkroom to observe whether the lens was cloudy or had any opaque material with the naked eyes.

No cloudiness: the lens was not cloudy and had no opaque material

Cloudiness: the lens was cloudy or had an opaque material (2) Impact Resistance

The impact resistance was measured as the potential energy of a weight that broke a specimen prepared in the form of a plate having a diameter of 80 mm and a thickness of 1.2 mm when steel balls having different weights were fallen thereto in a sequence from a light ball to a heavy ball at a height of 127 cm at a temperature of 20° C. according to the test standards of the US FDA.

Steel balls each having a weight of 16 g, 32 g, 65 g, 100 g, 200 g, or 300 g were used in the ball dropping test at various heights to measure the potential energy when the lens was broken.

Calculation Example 1: The potential energy (Ep) for 16 g and 127 cm according to the FDA standard $Ep=mgh=0.016 \times 9.8 \times 1.27=0.2(J)$ Calculation Example 2: The potential energy for 67 g and 127 cm according to the Industrial safety standards $Ep=mgh=0.067 \times 9.8 \times 1.27=0.83(J)$

TABLE 1

| | m-XDI composition | | Properties of the optical lens | |
|---|---|---|---|---|
| Diamine composition | 3-methylbenzylamine | Content of 3-methylbenzyl isocyanate | Cloudiness | Impact resistance (J) |
| Ex. 1-1 | 10 ppm | 6 ppm | x | 0.4 J |
| Ex. 1-2 | 100 ppm | 25 ppm | x | 0.8 J |
| Ex. 1-3 | 500 ppm | 49 ppm | x | 0.8 J |
| Ex. 1-4 | 1,000 ppm | 102 ppm | x | 1.2 J |
| Ex. 1-5 | 2,000 ppm | 189 ppm | x | 2.5 J |
| C. Ex. 1-1 | 0 ppm | <1 ppm | x | 0.2 J |
| C. Ex. 1-2 | 1 ppm | <1 ppm | x | 0.2 J |
| C. Ex. 1-3 | 5 ppm | <1 ppm | x | 0.2 J |
| C. Ex. 1-4 | 9 ppm | 4 ppm | ○ | 0.2 J |
| C. Ex. 1-5 | 2,010 ppm | 208 ppm | ○ | 2.5 J |
| C. Ex. 1-6 | 2,500 ppm | 320 ppm | ○ | 2.5 J |
| C. Ex. 1-7 | 3,000 ppm | 790 ppm | ○ | 2.5 J |

As can be seen from the above table, the optical lenses in Examples 1-1 to 1-5 of the present invention prepared by adding a specific content of the benzylmonoamine to the diamine composition had excellent impact resistance without the occurrence of cloudiness at the same time as compared with the optical lenses of Comparative Examples 1-1 to 1-7.

Specifically, the optical lenses in Examples 1-1 to 1-5 prepared by adding 3-methylbenzylamine to the diamine composition in an amount of 10 ppm to 2,000 ppm had no cloudiness and an excellent impact resistance of 0.4 J to 2.5 J.

In contrast, in Comparative Examples 1-1 to 1-4 in which the content of 3-methylbenzylamine was 5 ppm or less, the impact resistance was very low as 0.2 J although cloudiness did not occur.

In addition, in Comparative Example 1-5 in which the content of 3-methylbenzylamine was 9 ppm, the impact resistance was low as 0.2 J with the occurrence of cloudiness.

Meanwhile, in Comparative Examples 1-5 to 1-7 in which the content of 3-methylbenzylamine was excessive as it exceeded 2,000 ppm, cloudiness occurred although the impact resistance was good.

Accordingly, if an optical lens is prepared using a diamine composition in which an additive is added according to the embodiment of the present invention, the optical characteristics as well as mechanical properties of the lens are excellent. Thus, it is suitable for use as an optical lens of high quality.

Examples 2-1 to 2-5 and Comparative Examples 2-1 and 2-2

Step (1): Preparation of a Diamine Hydrochloride Composition

First, a diamine composition containing m-XDA was prepared, and the b* value according to the CIE color coordinate was measured. If the b* value exceeded 3.0, distillation was carried out under the conditions of 100° C. to 130° C. and 0.1 torr to 1 torr, such that the b* value was adjusted within a range of 0.01 to 3.0. A reactor was charged with 1,009.4 g (9.46 moles) of an aqueous solution of 35% hydrochloric acid, followed by lowering the internal temperature of the reactor to 15° C. with stirring. While the temperature of the reactor was maintained at 60° C., 600.0 g (4.4 moles) of the diamine composition prepared above was introduced for 1 hour. Upon completion of the introduction, the internal temperature of the reactor was lowered to 10° C., and it was stirred for 1 hour. Thereafter, 1,320.0 g of tetrahydrofuran (THF) was introduced, and the internal temperature of the reactor was lowered to −5° C., followed by stirring for 1 hour. Upon completion of the reaction, the diamine hydrochloride composition containing m-XDA·2HCl was separated by vacuum filtration using a filter, and the filtered tetrahydrofuran was recovered for reuse. In order to remove the residual solvent and water, the residual solvent and water were removed from the separated diamine hydrochloride composition at 90° C., and it was vacuum dried at 0.5 torr.

Step (2): Preparation of a Diisocyanate Composition

Reactor A was charged with 800 g of the diamine hydrochloride composition prepared above and 3,550 g of orthodichlorobenzene (ODCB), followed by heating them at about 125° C. with stirring. Reactor B was charged with 950 g of triphosgene (BTMC) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. Thereafter, it was cooled to 10° C., and the remaining solids were filtered using celite. The organic solvent (ODCB) was removed, and distillation was carried out to obtain a diisocyanate composition containing m-XDI. Here, the removal of the organic solvent was carried out for 8 hours at a pressure of 0.5 torr or less and a temperature of 60° C. In addition, the distillation was carried out for 10 hours at a pressure of 0.1 torr or less and a temperature of 120° C.

The b* values according to the CIE color coordinates of the diamine composition used as a starting material in the Examples and the Comparative Examples, the diamine hydrochloride composition, and the diisocyanate composition obtained in steps (1) and (2), respectively, are summarized in Table 2 below. A liquid sample was filled in a quartz cell having a thickness of 10 mm, and a solid sample was dissolved in an organic solvent (ODCB) at 8% by weight. The b* value was measured using a spectrophotometer (Colormate, Sinko Corporation).

TABLE 2

| | b* value | | |
|---|---|---|---|
| | Diamine composition | Diamine hydrochloride composition | Diisocyanate composition |
| Ex. 2-1 | 0.4 | 0.6 | 0.4 |
| Ex. 2-2 | 2.7 | 1.0 | 0.8 |
| Ex. 2-3 | 1.5 | 0.8 | 0.6 |
| Ex. 2-4 | 3.3 before distillation/ 0.5 after distillation | 0.7 | 0.5 |
| Ex. 2-5 | 4.5 before distillation/ 0.6 after distillation | 0.7 | 0.6 |
| C. Ex. 2-1 | 3.3 | 1.4 | 2.1 |
| C. Ex. 2-2 | 4.5 | 1.8 | 2.7 |

As can be seen from the above table, as the b* value according to the CIE color coordinate of the diamine composition was adjusted, the b* value of the diamine hydrochloride composition and the diisocyanate composition could be changed.

Preparation of an Optical Lens 49.3 parts by weight of 4,8-bis(mercaptomethyl)-3,6,9-trithiaundecane-1,11-dithiol, 50.7 parts by weight of the m-XDI composition prepared in the Examples or the Comparative Examples, 0.01 part by weight of dibutyltin dichloride, and 0.1 part by weight of a phosphate ester release agent (ZELEC™ UN Stepan) were homogeneously mixed, which was defoamed at 600 Pa for 1 hour, filtered through a Teflon filter of 3 µm, and injected into a mold made of a glass mold and a tape. The mold was maintained at 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens.

Evaluation Method

Evaluation methods for the Examples and the Comparative Examples are as follows.

(1) Distillation Yield

The distillation yield was calculated by measuring the amount of the diisocyanate composition upon the distillation relative to the theoretical amount of the diisocyanate composition produced from the amounts of the diamine hydrochloride composition introduced to the reaction with triphosgene.

(2) Content of a Diisocyanate

The content of a diisocyanate in the diisocyanate composition was determined by gas chromatography (GC) (instrument: 6890/7890 of Agilent, carrier gas: He, injection temperature 250° C., oven temperature 40° C. to 320° C., column: HP-1, Wax, 30 m, detector: FID, 300° C.)

(3) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(4) Cloudiness (Haze)

The optical lens was irradiated to a projector in a darkroom to observe whether the optical lens was cloudy or had any opaque material with the naked eyes.

(5) Transmittance and Yellow Index (Y.I.)

An optical lens was prepared in the form of a cylinder with a radius of 16 mm and a height of 45 mm. Light was transmitted in the height direction to measure the yellow index and transmittance. The yellow index was calculated by the following equation based on the values of x and y, which are the measurement results. Y.I.=(234x+106y)/y.

TABLE 3

| | | Diisocyanate composition | | | | | |
|---|---|---|---|---|---|---|---|
| | | Diisocyanate content (% by weight) | | | | | |
| | Distillation yield | Before distillation | After distillation | | Optical lens | | |
| | | | | Stria | Cloudiness | Transmittance | Y.I. |
| Ex. 2-1 | 91% | 99.1 | 99.9 | Absent | Absent | 90% | 19 |
| Ex. 2-2 | 88% | 99.0 | 99.9 | Absent | Absent | 91% | 22 |
| Ex. 2-3 | 90% | 99.1 | 99.9 | Absent | Absent | 89% | 20 |
| Ex. 2-4 | 90% | 99.1 | 99.9 | Absent | Absent | 91% | 21 |
| Ex. 2-5 | 91% | 99.1 | 99.9 | Absent | Absent | 91% | 21 |
| C. Ex. 2-1 | 85% | 98.5 | 99.8 | Absent | Slight cloudiness | 90% | 25 |
| C. Ex. 2-2 | 83% | 98.4 | 99.7 | Absent | Slight cloudiness | 88% | 29 |

As can be seen from Tables 2 and 3 above, in Examples 2-1 to 2-5 in which a diisocyanate composition was prepared using a diamine composition having a b* value in the preferred range, the yield and purity were excellent, and the optical lenses had high transmittance without the occurrence of stria, cloudiness, and yellowing. In contrast, in Comparative Examples 2-1 and 2-2 in which a diisocyanate composition was prepared using a diamine composition having a b* value falling outside the preferred range, the yield and purity were relatively poor, and the optical lenses had the occurrence of cloudiness and yellowing.

The invention claimed is:

1. A process for preparing a diisocyanate composition, which comprises:
    reacting a diamine composition with an aqueous hydrochloric acid solution to obtain a diamine hydrochloride composition; and
    obtaining a diisocyanate composition by reacting the diamine hydrochloride composition with triphosgene,
    wherein the diamine composition comprises a diamine; and a benzylmonoamine having a methyl group in an amount of 10 ppm to 2,000 ppm based on the total amount of the diamine composition, and wherein after the reaction of the diamine composition and the aqueous hydrochloric acid solution, a first organic solvent is further added to obtain the diamine hydrochloride composition in a solid phase, wherein the reaction of the diamine hydrochloride composition with triphosgene is carried out in a second organic solvent, wherein the second organic solvent is introduced to the reaction in an amount of 3 to 5 times of the weight of the diamine hydrochloride composition, wherein the first organic solvent is at least one selected from the group consisting of diethyl ether, diisopropyl ether, dioxane, tetrahydrofuran, methanol, ethanol, dimethyl sulfoxide, dimethylformamide, acetonitrile, acetone, trichloroethylene, tetrachloroethane, trichloroethanol, n-butanol, isobutanol, methyl ethyl ketone, methyl butyl ketone, isopropanol, hexane, chloroform, and methyl acetate, wherein the second organic solvent is at least one selected from the group consisting of benzene, toluene, ethylbenzene, chlorobenzene, monochlorobenzene, 1,2-dichlorobenzene, dichloromethane, 1-chloro-n-butane, 1-chloro-n-pentane, 1-chloro-n-hexane, chloroform, carbon tetrachloride, n-pentane, n-hexane, n-heptane, n-octane, cyclohexane, cyclopentane, cyclooctane, and methylcyclohexane.

2. The process for preparing a diisocyanate composition of claim 1, wherein the diamine hydrochloride composition comprises a benzylmonoamine hydrochloride having a methyl group, the benzylmonoamine hydrochloride having a methyl group is reacted with triphosgene to produce a benzyl isocyanate having a methyl group, the benzyl isocyanate having a methyl group is contained in the diisocyanate composition in an amount of 5 ppm to 200 ppm based on the amount of the diisocyanate composition, and the ratio of the content of the benzyl isocyanate having a methyl group to the content of the benzylmonoamine having a methyl group which remains unconverted in the diisocyanate composition is 0.05 to 0.9.

3. The process for preparing a diisocyanate composition of claim 2, which further comprises distilling the reaction resultant obtained by reacting the diamine hydrochloride composition and triphosgene, and the distillation comprises a first distillation at 40° C. to 60° C. for 2 hours to 8 hours and a second distillation at 100° C. to 120° C. for 2 to 10 hours.

4. The process for preparing a diisocyanate composition of claim 1, wherein the diamine hydrochloride composition and triphosgene are introduced to the reaction at an equivalent ratio of 1:1 to 5, and the reaction of the diamine hydrochloride composition and triphosgene is carried out at a temperature of 110° C. to 160° C.

* * * * *